(12) United States Patent
Delucia et al.

(10) Patent No.: US 9,872,626 B2
(45) Date of Patent: Jan. 23, 2018

(54) PRINTED CIRCUIT BOARD ASSEMBLY WITH FERRITE FOR MEDICAL DEVICE

(71) Applicant: Welch Allyn, Inc., Skaneateles Falls, NY (US)

(72) Inventors: Paul Delucia, Baldwinsville, NY (US); Alan S. Knieriem, Baldwinsville, NY (US); David M. Babson, Warners, NY (US); David M. Fallat, Auburn, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 35 days.

(21) Appl. No.: 14/934,783

(22) Filed: Nov. 6, 2015

(65) Prior Publication Data

US 2016/0135287 A1    May 12, 2016

Related U.S. Application Data

(60) Provisional application No. 62/076,878, filed on Nov. 7, 2014.

(51) Int. Cl.
| | |
|---|---|
| *A61B 5/022* | (2006.01) |
| *A61B 5/021* | (2006.01) |
| *H05K 1/02* | (2006.01) |
| *A61B 5/0205* | (2006.01) |
| *A61B 5/00* | (2006.01) |

(Continued)

(52) U.S. Cl.
CPC ......... *A61B 5/02233* (2013.01); *A61B 5/002* (2013.01); *A61B 5/0235* (2013.01); *A61B 5/02055* (2013.01); *A61B 5/02141* (2013.01); *A61B 5/742* (2013.01); *A61B 5/7405* (2013.01); *A61B 50/13* (2016.02); *G02F 1/133308* (2013.01); *H02J 1/00* (2013.01); *H02J 7/0054* (2013.01); *H05K 1/0216* (2013.01); *H05K 1/0296* (2013.01); *A61B 2560/0204* (2013.01); *A61B 2562/12* (2013.01); *A61B 2562/166* (2013.01); *G02F 2001/13332* (2013.01); *G02F 2001/133325* (2013.01); *H05K 1/183* (2013.01); *H05K 2201/0715* (2013.01); *H05K 2201/09063* (2013.01); *H05K 2201/1003* (2013.01)

(58) Field of Classification Search
None
See application file for complete search history.

(56) References Cited

U.S. PATENT DOCUMENTS

| | | | | |
|---|---|---|---|---|
| 4,455,545 | A * | 6/1984 | Shelly | ............... H01F 5/003 336/178 |
| 4,716,389 | A * | 12/1987 | Gawronski | ............ H01P 1/227 333/246 |

(Continued)

OTHER PUBLICATIONS

International Search Report and Written Opinion in PCT/US2015/059516, dated Mar. 17, 2016, 13 pages.

*Primary Examiner* — Dimary Lopez Cruz
*Assistant Examiner* — Muhammed Azam
(74) *Attorney, Agent, or Firm* — Merchant & Gould P.C.

(57) ABSTRACT

A printed circuit board assembly includes a printed circuit board and a ferrite. The printed circuit board has a substantially planar top surface and a substantially planar bottom surface. The ferrite has an annular cross section that defines a channel. The ferrite is positioned on the printed circuit board such that a portion of the plurality of traces passes through the channel.

19 Claims, 28 Drawing Sheets

(51) Int. Cl.
  *H02J 1/00* (2006.01)
  *H02J 7/00* (2006.01)
  *G02F 1/1333* (2006.01)
  *H05K 1/18* (2006.01)
  *A61B 5/0235* (2006.01)
  *A61B 50/13* (2016.01)

(56) References Cited

U.S. PATENT DOCUMENTS

| | | | |
|---|---|---|---|
| 4,789,224 A | 12/1988 | Bougsty | |
| 4,796,079 A * | 1/1989 | Hettiger | H01P 1/227 174/260 |
| 4,864,486 A * | 9/1989 | Spreen | H01F 27/2804 336/175 |
| 4,873,757 A * | 10/1989 | Williams | H01F 17/0013 29/602.1 |
| 5,025,211 A * | 6/1991 | Craft | G01R 1/18 333/12 |
| 5,136,120 A * | 8/1992 | Craft | G01R 1/18 174/260 |
| 5,321,380 A * | 6/1994 | Godek | H01F 17/0006 174/260 |
| 5,339,178 A | 8/1994 | Phelps, III et al. | |
| 5,353,001 A * | 10/1994 | Meinel | H01F 17/0006 29/602.1 |
| 5,422,751 A | 6/1995 | Lewis et al. | |
| 5,455,552 A * | 10/1995 | Metsler | H01F 27/29 333/185 |
| 5,469,334 A * | 11/1995 | Balakrishnan | H01F 17/0033 174/529 |
| 5,528,025 A * | 6/1996 | Swintek | G06K 7/0008 235/375 |
| 5,565,837 A * | 10/1996 | Godek | H01F 17/0006 174/250 |
| 5,603,847 A * | 2/1997 | Howard | H05K 1/162 216/17 |
| 5,631,822 A * | 5/1997 | Silberkleit | H01F 27/2804 336/200 |
| 5,748,270 A | 5/1998 | Smith | |
| 5,774,028 A * | 6/1998 | Kim | H01G 4/40 333/181 |
| 5,801,597 A * | 9/1998 | Carter | H01F 17/0006 333/12 |
| 5,801,602 A * | 9/1998 | Fawal | H01F 17/0006 333/177 |
| 5,892,412 A * | 4/1999 | Norte | H01P 1/215 333/24.1 |
| 5,896,079 A * | 4/1999 | Parker | H01F 17/06 336/172 |
| 5,949,321 A * | 9/1999 | Grandmont | H01F 17/0006 336/200 |
| 5,952,909 A * | 9/1999 | Umeno | H01F 17/0013 29/602.1 |
| 5,975,711 A | 11/1999 | Parker et al. | |
| 6,000,128 A * | 12/1999 | Umeno | H01F 27/2804 29/605 |
| 6,028,500 A * | 2/2000 | Buist | H01F 27/263 336/100 |
| 6,089,917 A * | 7/2000 | Anderson | H05K 1/0233 439/620.06 |
| 6,116,924 A * | 9/2000 | Laut | H01R 23/6873 361/818 |
| 6,147,583 A * | 11/2000 | Rinne | H01F 27/2804 336/200 |
| 6,147,928 A * | 11/2000 | Onizuka | H01F 17/06 367/23 |
| 6,181,404 B1 * | 1/2001 | Gaffney | G02F 1/13452 349/149 |
| 6,195,269 B1 * | 2/2001 | Hino | H01F 17/06 174/350 |
| 6,288,626 B1 * | 9/2001 | Cameron | H01F 17/0013 336/200 |
| 6,335,671 B1 * | 1/2002 | Roessler | H01F 27/292 336/192 |
| 6,356,182 B1 * | 3/2002 | Nagashima | H01F 27/2804 336/200 |
| 6,587,166 B1 | 7/2003 | Lee et al. | |
| 6,741,155 B2 * | 5/2004 | Usui | H01F 3/14 336/200 |
| 6,911,889 B2 * | 6/2005 | Bodley | H01P 1/215 29/602.1 |
| 7,327,430 B2 | 2/2008 | Lee et al. | |
| 7,391,137 B2 * | 6/2008 | Gottmann | H02K 11/024 310/51 |
| 7,405,925 B2 | 7/2008 | Sung | |
| 7,535,537 B2 | 5/2009 | Lee et al. | |
| 7,545,453 B2 | 6/2009 | Kim | |
| 7,843,526 B2 | 11/2010 | Lee et al. | |
| 7,864,263 B2 | 1/2011 | Kim | |
| 7,883,369 B1 * | 2/2011 | Sun | H01R 23/6873 439/607.35 |
| 7,954,360 B2 | 6/2011 | Asher et al. | |
| 8,077,006 B2 * | 12/2011 | Mui | H01P 5/10 29/602.1 |
| 8,203,659 B2 | 6/2012 | Chou | |
| 8,253,914 B2 | 8/2012 | Kajiya et al. | |
| 8,345,179 B2 | 1/2013 | Mo et al. | |
| 8,354,894 B2 * | 1/2013 | Mui | H01F 3/12 333/124 |
| 8,384,841 B2 | 2/2013 | Lin et al. | |
| 8,736,802 B2 | 5/2014 | Kajiya et al. | |
| 2001/0017576 A1 * | 8/2001 | Kondo | H03F 1/56 333/24.2 |
| 2002/0070835 A1 * | 6/2002 | Dadafshar | H01F 27/027 336/200 |
| 2002/0070836 A1 * | 6/2002 | Fujiyoshi | H01F 27/2852 336/200 |
| 2002/0089405 A1 * | 7/2002 | Jitaru | H01F 27/2804 336/200 |
| 2002/0159214 A1 * | 10/2002 | Perlick | H01F 27/06 361/160 |
| 2002/0170745 A1 * | 11/2002 | Opitz | H01F 17/0013 174/255 |
| 2002/0173202 A1 * | 11/2002 | Okamoto | H01R 13/65802 439/607.36 |
| 2003/0026962 A1 * | 2/2003 | Kawai | H01F 17/06 428/209 |
| 2004/0012729 A1 | 1/2004 | Kim | |
| 2004/0090567 A1 | 5/2004 | Lee et al. | |
| 2004/0113739 A1 * | 6/2004 | Du | H01F 30/10 336/200 |
| 2004/0133092 A1 * | 7/2004 | Kain | A61B 5/0031 600/377 |
| 2004/0257190 A1 * | 12/2004 | Peck | H01F 27/2847 336/212 |
| 2005/0174207 A1 * | 8/2005 | Young | H01F 17/0006 336/200 |
| 2006/0158294 A1 * | 7/2006 | Meadors | H01F 17/06 336/83 |
| 2008/0079524 A1 * | 4/2008 | Suzuki | H01F 27/2804 336/61 |
| 2008/0087072 A1 | 4/2008 | Asher et al. | |
| 2008/0111942 A1 | 5/2008 | Lee et al. | |
| 2009/0026841 A1 | 1/2009 | Nakanishi | |
| 2009/0256989 A1 | 10/2009 | Lee et al. | |
| 2009/0295529 A1 * | 12/2009 | Silva | H01F 3/10 336/213 |
| 2011/0019121 A1 | 1/2011 | Mo et al. | |
| 2011/0058355 A1 | 3/2011 | Teng et al. | |
| 2011/0102701 A1 | 5/2011 | Teng et al. | |
| 2011/0204720 A1 | 8/2011 | Ruiz et al. | |
| 2011/0261281 A1 | 10/2011 | Liu et al. | |
| 2012/0099044 A1 | 4/2012 | Lin et al. | |
| 2012/0120339 A1 | 5/2012 | Kim et al. | |
| 2012/0193983 A1 | 8/2012 | Yukizane | |
| 2012/0197340 A1 * | 8/2012 | Tesfayesus | A61N 1/3601 607/42 |
| 2012/0267437 A1 | 10/2012 | Jain et al. | |
| 2014/0039351 A1 | 2/2014 | Mix et al. | |

(56) References Cited

U.S. PATENT DOCUMENTS

| | | |
|---|---|---|
| 2014/0132877 A1 | 5/2014 | Tsao et al. |
| 2016/0128585 A1 | 5/2016 | Knieriem |
| 2016/0131935 A1 | 5/2016 | Knieriem |
| 2016/0134107 A1 | 5/2016 | Fallat |
| 2016/0135287 A1* | 5/2016 | Delucia ............... A61B 5/02233 600/300 |

* cited by examiner

PRINTED CIRCUIT BOARD ASSEMBLY WITH FERRITE FOR MEDICAL DEVICE

BACKGROUND

Medical devices can include displays, pumps, batteries and printed circuit boards. As those components are made smaller and the device size decreases, design costs and repair costs can increase. Additionally, some components can cause electromagnetic interference that can detract from the performance of the medical device.

DETAILED DESCRIPTION

Health care environments can include hospitals, clinics, managed care facilities, and other locations where medical care is provided. Medical personnel in health care environments can utilize vital signs monitoring devices, vital signs displays, personal computing devices and electronic medical record access portals. Medical staff and providers often need to record a patient's vital signs and enter those vital signs into the patient's electronic medical record. Currently, providers must perform vital signs measurements, remember the measurements, and then enter those measurements into one or more computing devices which may or may not be directly linked to the patient's electronic medical record.

Figure 1:
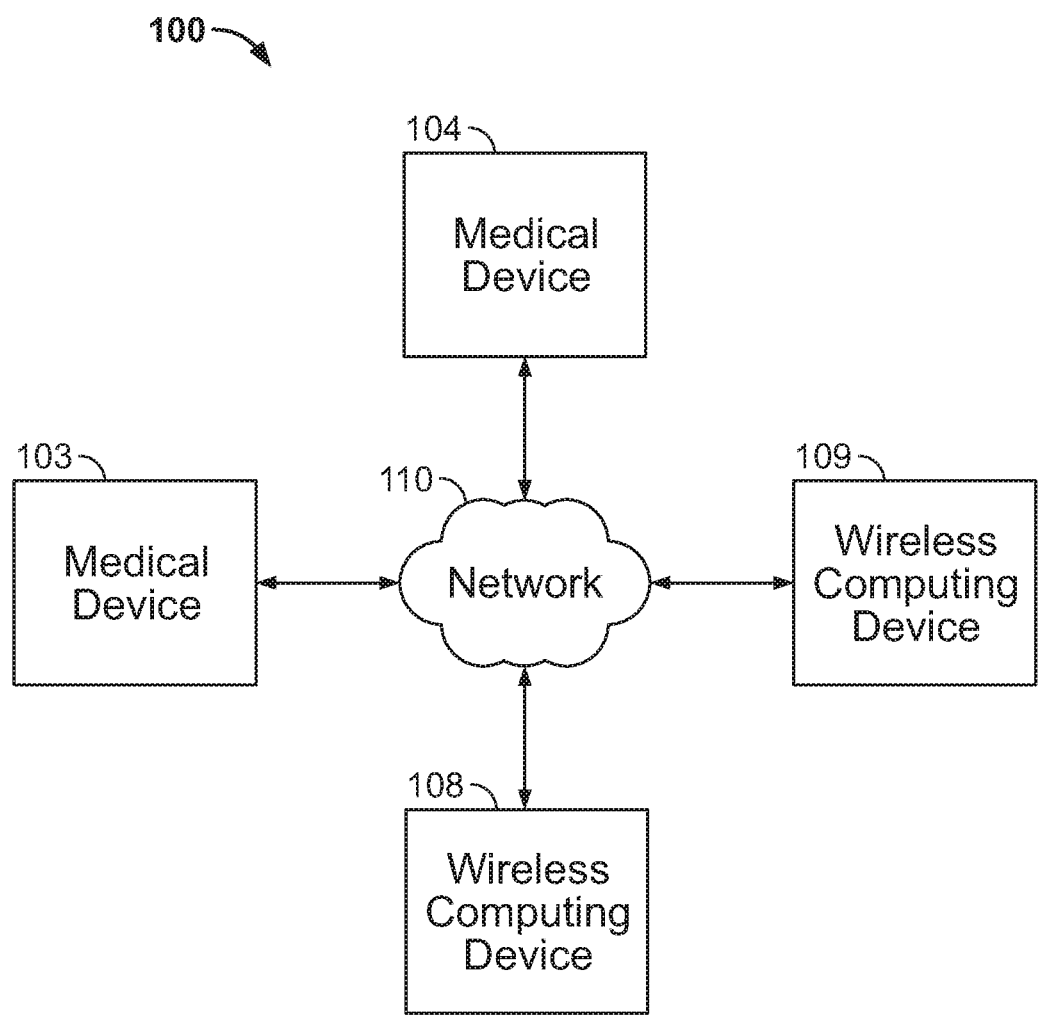
FIG. 1 a block diagram of a wireless healthcare system.

FIG. 1 illustrates a block diagram of an example wireless health care network 110. The example network 110 includes medical devices 103 and 104, wireless computing devices 108 and 109, and communication network 110. In embodiments, the example network 110 can include more or fewer medical devices 103 and 104. In embodiments, the example network can include more or fewer wireless computing devices 108 and 109. The communication network 110 can be a wireless network, such as WiFi, Bluetooth, Zigbee, Ant, Z-Wave, etc.

In some embodiments, the one or more medical devices 103 and 104 can include one or more vital signs measurement components. For example, the medical devices 103 can include, for example, a thermometer, a heart rate monitor, a pulse oximeter, a non-invasive blood pressure monitor, and a respiration rate monitor. In embodiments, one or more vital signs measurement components are wirelessly linked to the medical devices 103 and 104 and can transmit measurements to the medical devices 103 and 104.

Example computing components of medical devices 103 and 104 are shown and described in more detail with reference to FIG. 9, below.

In some embodiments, the one or more wireless computing devices 108 and 109 can be smart phones, tablet computers, personal digital assistants, laptop computers, and desktop computers, which can optionally be mounted on portable carts. Example computing components of the one or more wireless computing devices 108 and 109 are shown and described in more detail with reference to FIG. 9, below. The use of less complicated wireless computing devices 108 and 109, such as heart rate monitors, pulse oximeters, etc., is also contemplated by this document.

Figure 2:
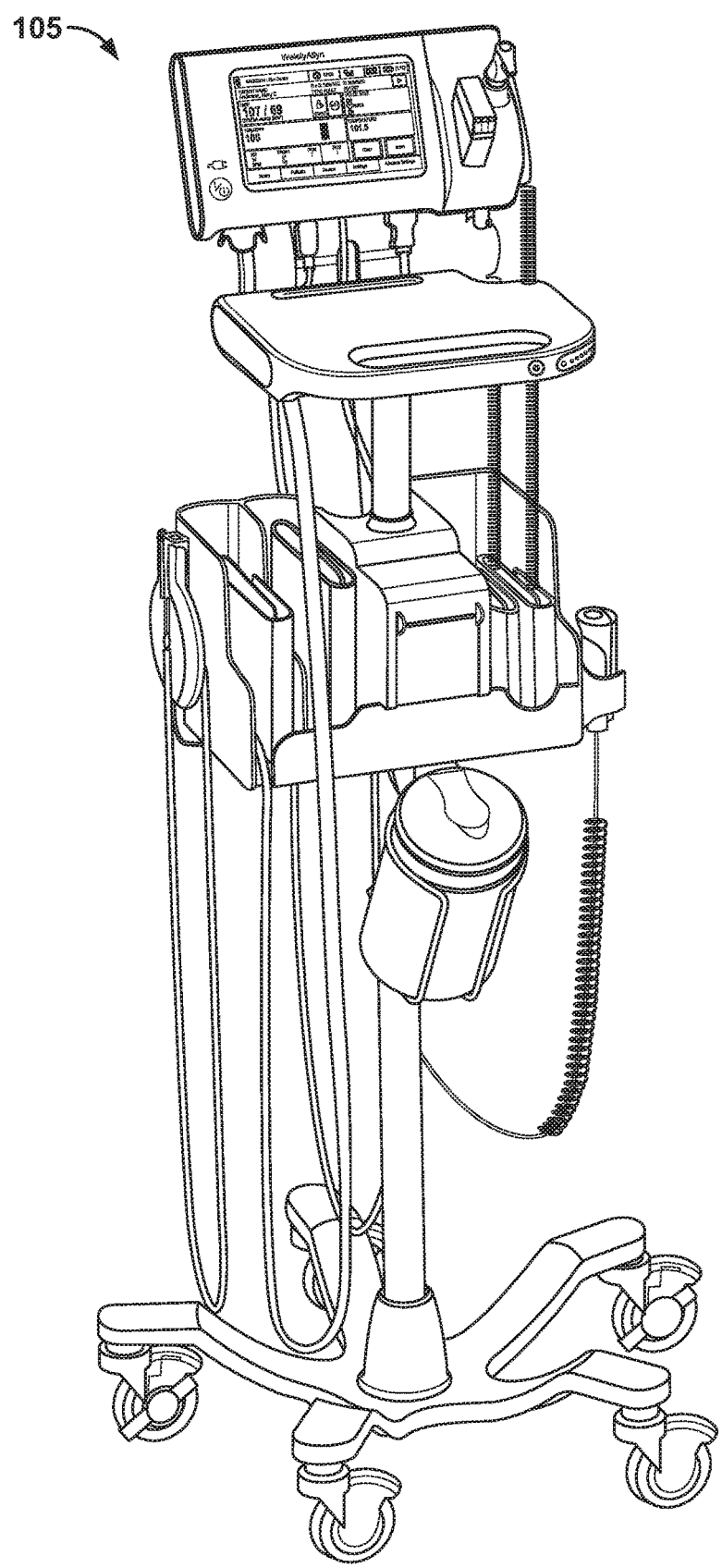
FIG. 2 illustrates an example medical device of FIG. 1.
Figure 3:
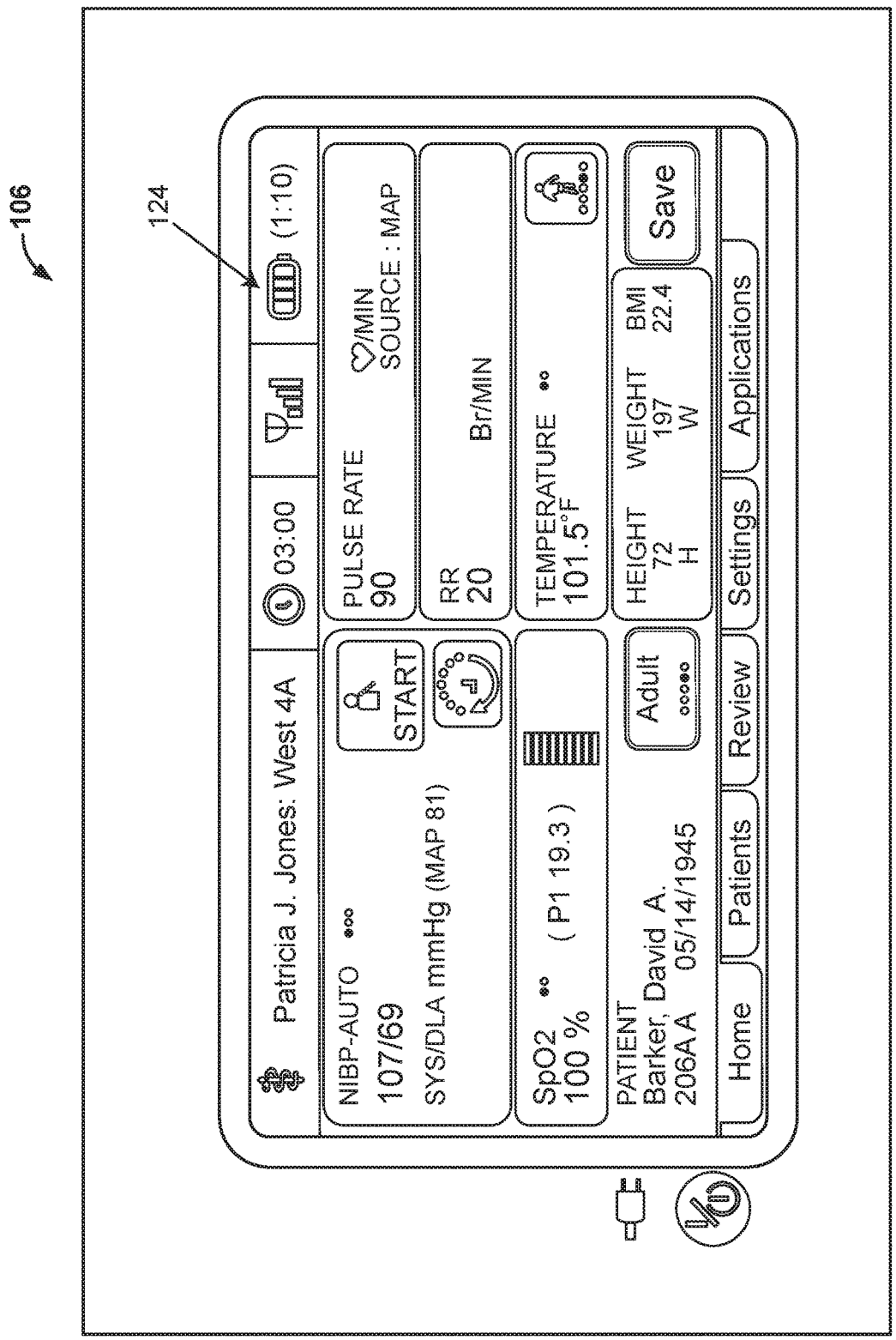
FIG. 3 illustrates another example medical device of FIG. 1.

FIG. 2 illustrates one example of the medical device 105. The medical device 105 is shown on a mobile cart, and the medical device 105 is programmed to provide the functionalities described herein, which can include, but are not limited to, vital signs monitoring. The medical device 105 includes a user interface, such as a touch screen, and includes the ability to execute multiple workflows or profiles. In some embodiments, the medical devices 105 and 106 in FIGS. 2 and 3 are the medical device 103 or 104 shown in, and described with reference to, FIG. 1. Other embodiments can include more or fewer components than those shown in FIG. 2, or include different components that accomplish the same or a similar function.

The medical device 105 is able to operate within one or more profiles. A profile is a series of one or more tasks that a user of the medical device 105 performs. When the medical device 105 operates within a profile, the medical device 105 provides functionality suitable for assisting the user in performing the profile. When the medical device 105 operates within different profiles, the medical device 105 provides different functionality.

When the medical device 105 is manufactured, the medical device 105 is configured to be able to operate within one or more profiles. After the medical device 105 is manufactured, the medical device 105 can be reconfigured to operate within one or more additional profiles. In this way, a user can adapt the medical device 105 for use in different profiles as needed.

In various embodiments, the medical device 105 operates within various profiles. For example, in some embodiments, the medical device 105 can operate within a monitoring profile or a non-monitoring profile. Example types of non-monitoring profiles include, but are not limited to, a spot check profile and an office profile. An example of a monitoring profile includes, but is not limited to, an intervals profile.

An additional example of the medical device 106 is shown in FIG. 3. In this example, the medical device 106 is similar to that of the medical device 105 described above. In embodiments, the medical device 106 is mounted on a wall. The medical device 106 is programmed in a manner similar to that described above to monitor physiological parameters of a patient. In some embodiments, the medical device 106 is a stand-alone device, which can mean that is not part of a mobile cart and it is not part of a wall-mounted station.

In the examples described herein, the medical devices 104, 105, 106 are computing devices that have been programmed to perform special, complex functions. These specially-programmed devices function to manipulate and provide data to the users in an improved form factor and with greater efficiency.

For example, as described further below, the medical devices 104, 105, 106 are specially programmed to provide the user with an improved interface that allows the user to discern important information at a glance. This improved interface removes unnecessary information and controls so that the data that is important can be more efficiently and easily viewed, particularly when the user is positioned at a distance from the medical device.

In the examples described herein, the medical devices 104, 105, 106 are computing devices that have been programmed to perform special, complex functions. These specially-programmed devices function to manipulate and provide data to the users in an improved form factor and with greater efficiency.

For example, as described further below, the medical devices 104, 105, 106 are specially programmed to provide the user with an improved interface during initial use of the devices. This allows the user to more efficiently select a profile for controlling the functionality of the device.

In addition, the medical devices 104, 105, 106 are specially programmed to assist the users once vital signs information is captured from the patients. For example, the devices are programmed to more efficiently and easily capture additional contextual information that is needed when saving vital signs data to a permanent record, such as an EMR record. This is accomplished using an interface that is more intuitive and robust.

The medical devices 104 and 105 shown in FIGS. 2 and 3 are only examples of a medical device. In some examples described herein, the medical devices 104 and 105 are portable devices. In other examples, the medical devices 104 and 105 are non-portable devices, such as computing devices like workstations. All different types of medical devices used to collect patient data can be used. Many configurations are possible.

Figure 4:
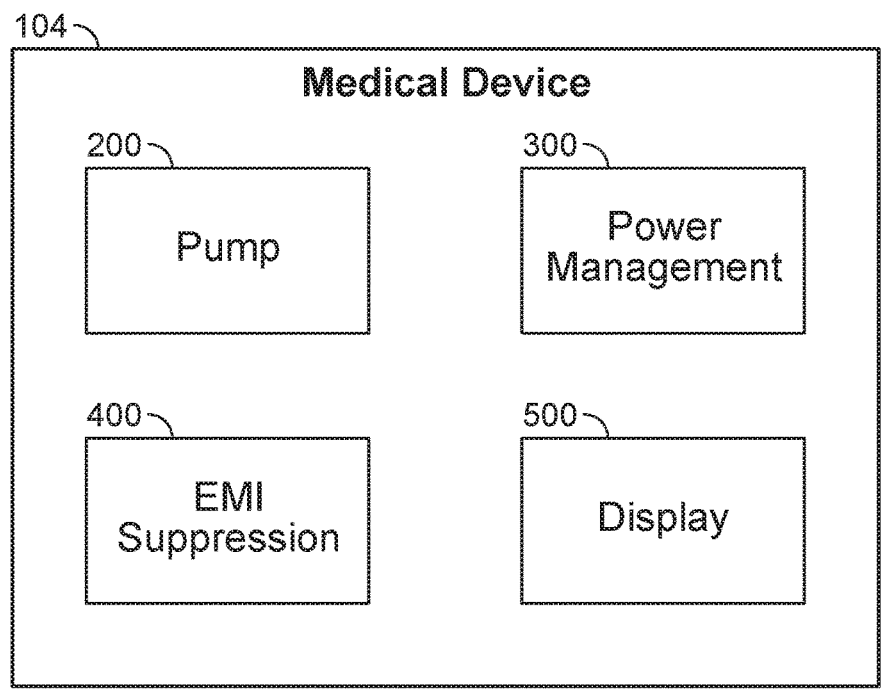
FIG. 4 illustrates a block diagram of an example medical device.

An example medical product system 100 is shown in FIG. 4. The example medical product system 100 includes the medical device 104 that can have a carrier assembly 200, power management module 300, electromagnetic interference (EMI) suppression module 400, and display 500. Other embodiments may include more or fewer components.

Figure 5:
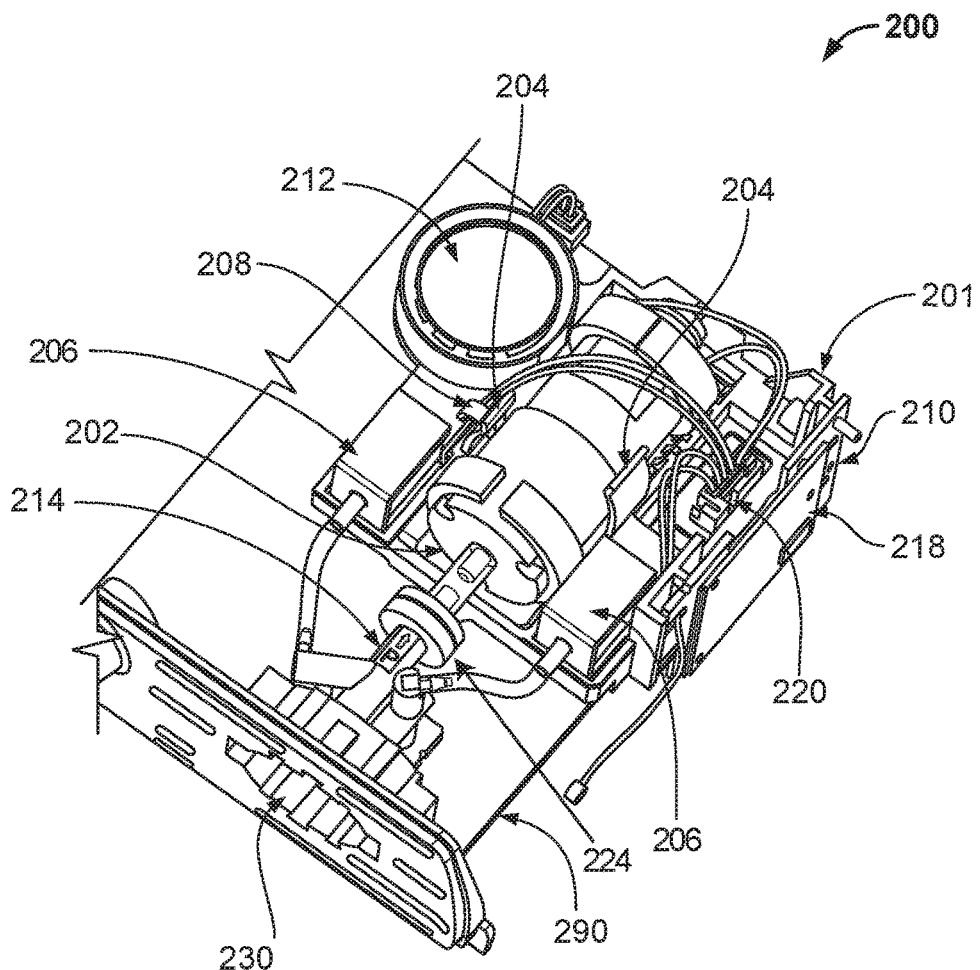
FIG. 5 illustrates the components of an example carrier assembly.
Figure 6:
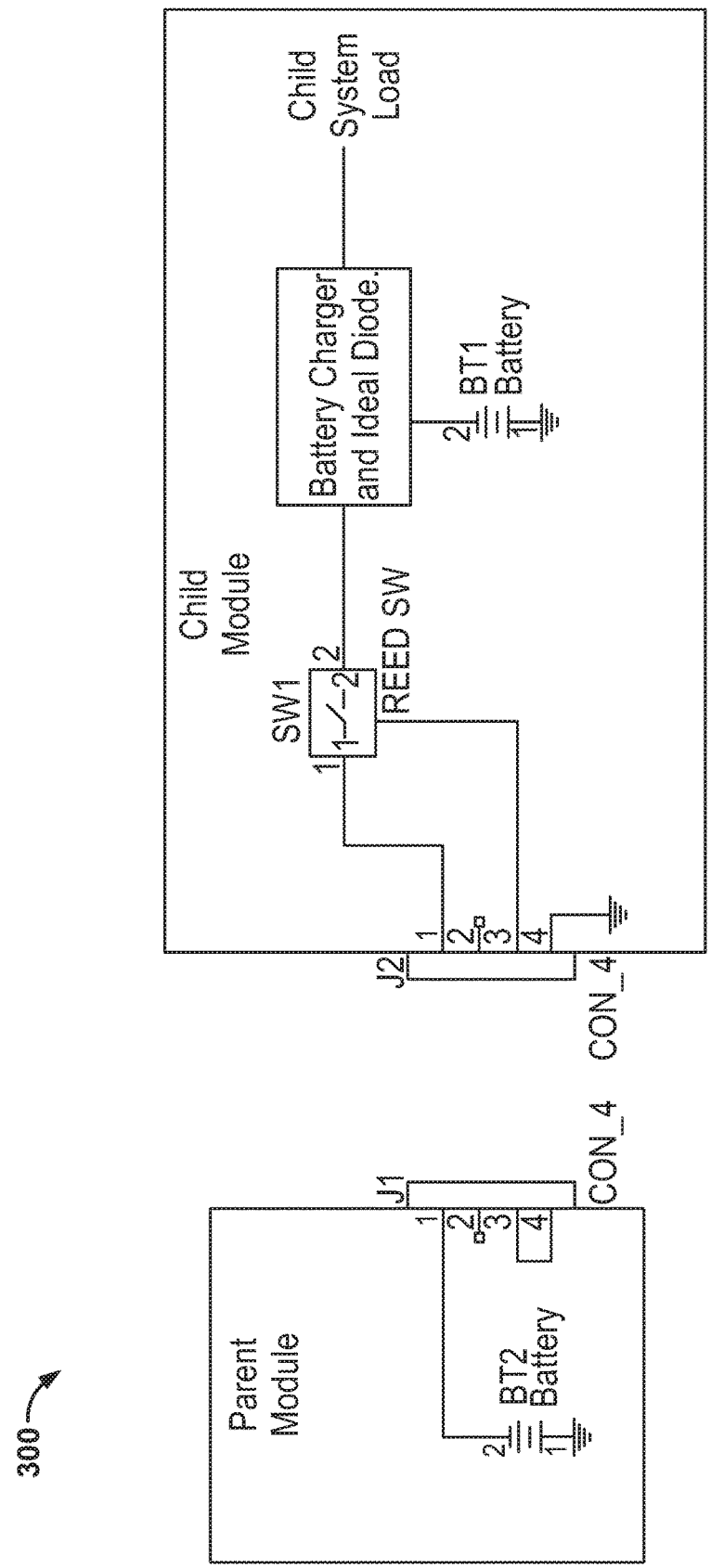
FIG. 6 illustrates an example power management system.
Figure 7:
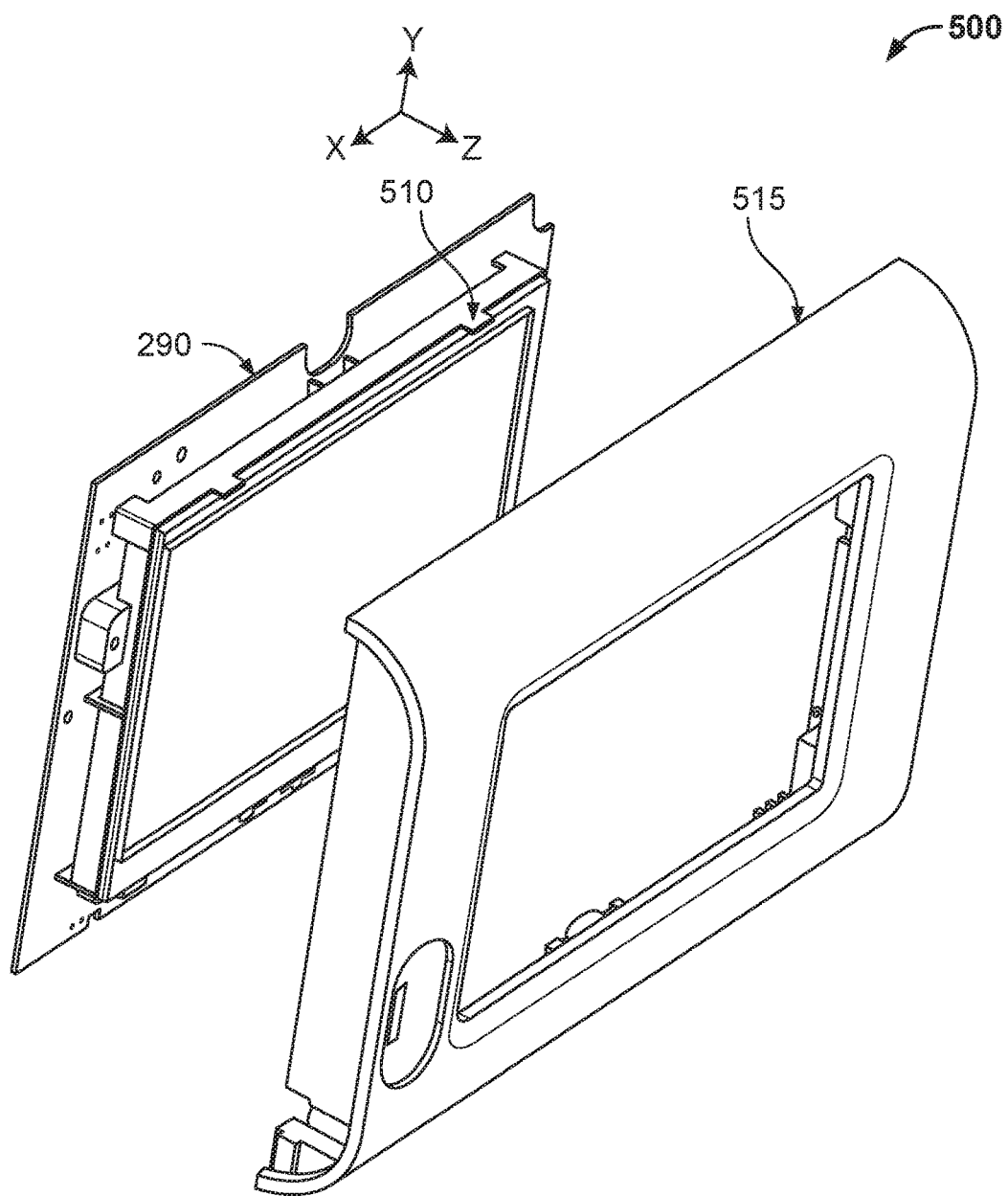
FIG. 7 illustrates example components of a display.
Figure 8:
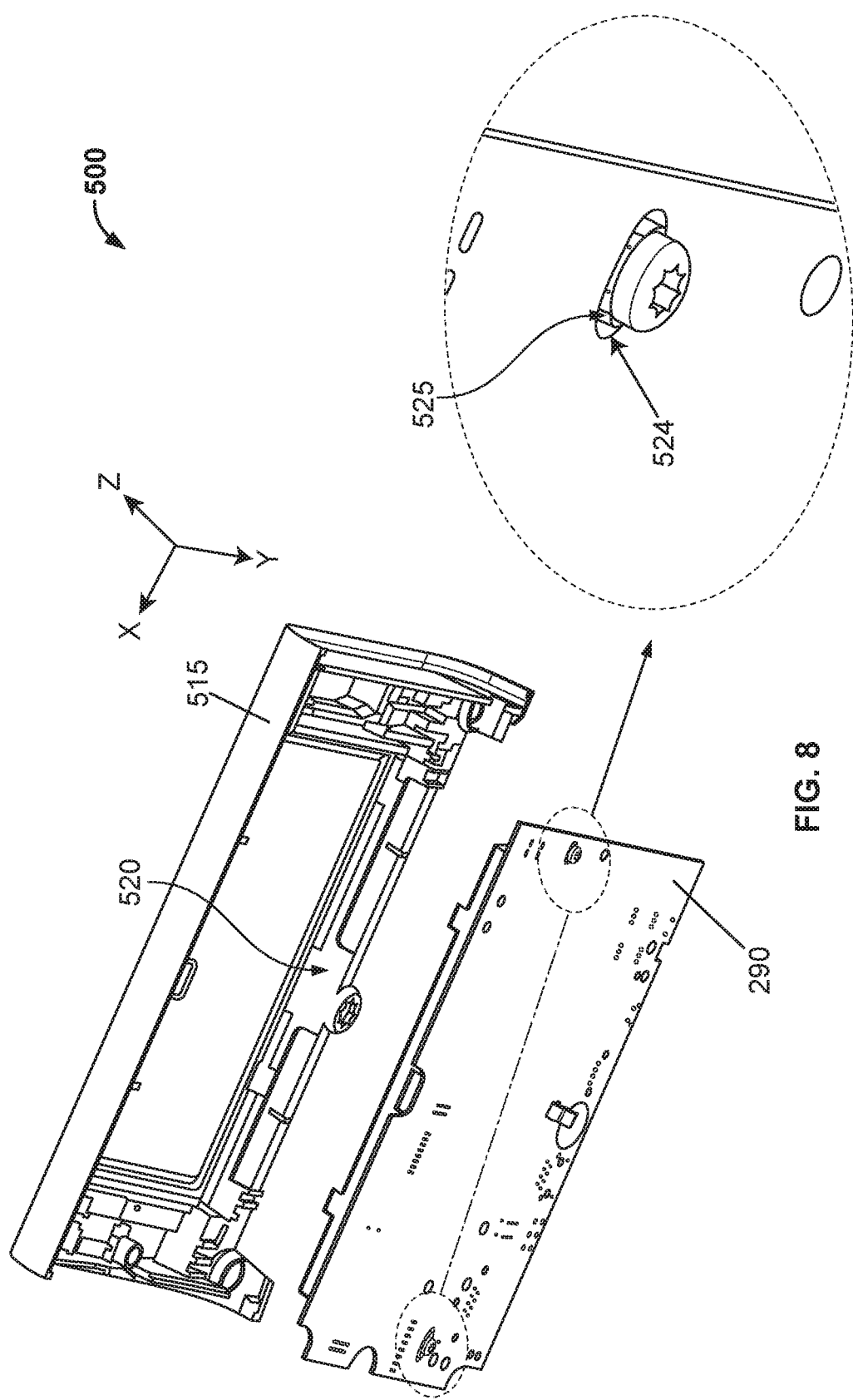
FIG. 8 illustrates a different view of the components shown in FIG. 7.
Figure 20:
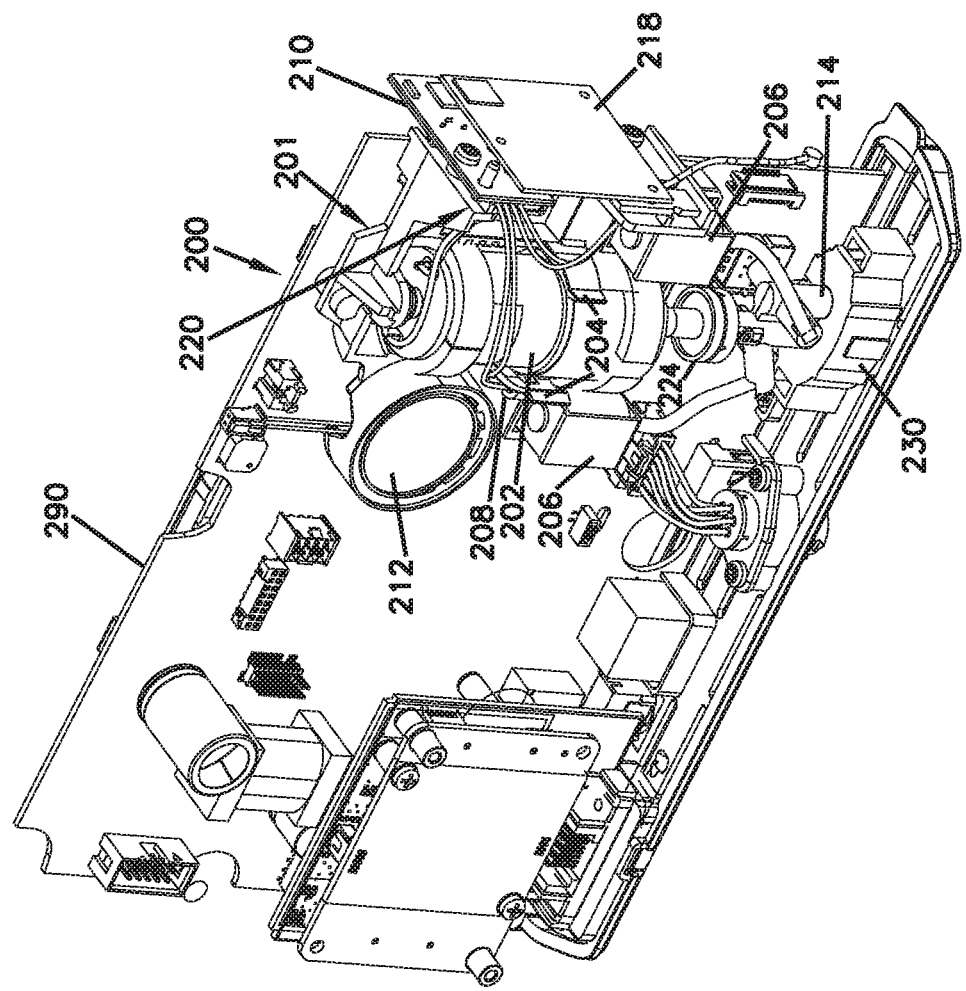
FIG. 20 illustrates an embodiment of the example carrier assembly shown in FIG. 5 mounted to an example main printed circuit assembly.
Figure 21:
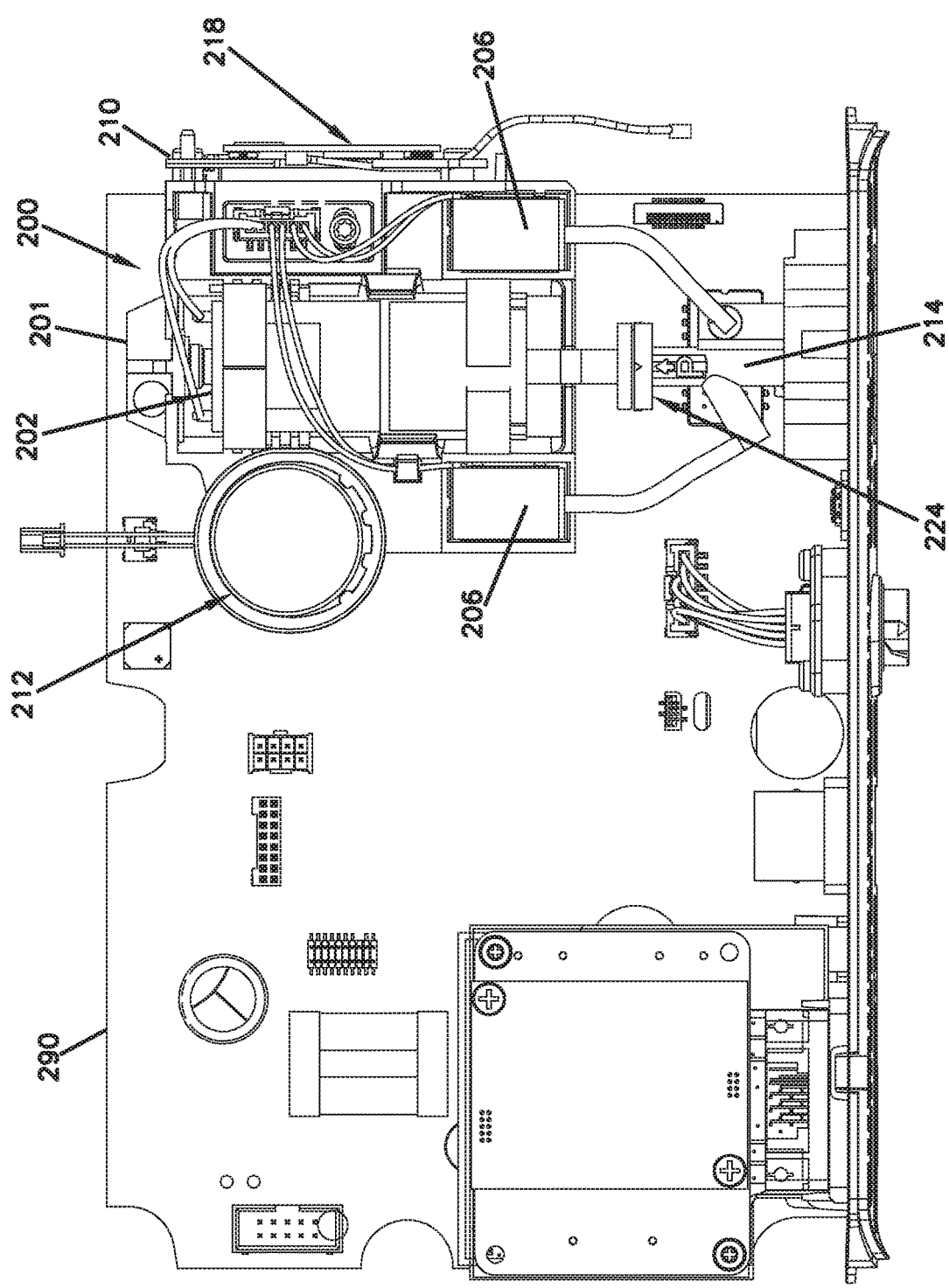
FIG. 21 illustrates a top plan view of the embodiment shown in FIG. 20.

FIG. 5 illustrates an example embodiment of the carrier assembly 200 that can be mounted to a main printed circuit assembly (PCA) 290 of the medical device 104. FIGS. 20 and 21 illustrate the example embodiment of carrier assembly 200 mounted to a PCA 290. The example assembly 200 can include a plastic carrier 201 supporting a pump 202, pump retention snaps 204, valves 206, a wire routing feature 208, a WiFi radio 210, a Bluetooth radio 218, a speaker 212, and an integrated pump/valve harness 220. A manifold 214 can be in communication with the pump 202 and a blood pressure (BP) cuff port 230. FIGS. 20 and 21 illustrate embodiments of a main printed circuit assembly 290 including the example embodiment of carrier assembly 200. Other embodiments can include more or fewer components.

The example carrier assembly 200 consolidates the blood pressure pneumatic system that includes a pump 202, a solenoid valve 206 and a check valve 224. The pneumatic system can be supported by a plastic carrier 201. As shown, the main printed circuit assembly 290 has a top surface area that supports and houses various components, including the carrier assembly 200. The carrier assembly 200 occupies an amount of surface area on the top surface area of the main printed circuit assembly 290 that is at least less than 50% of the top surface area; at least less than 40% of the top surface area; at least less than 33% of the top surface area; at least less than 25% of the top surface area; or at least less than 20% of the top surface area.

In embodiments, the pump 202, solenoid valve 206 and check valve 224 are all in fluid communication with each other and with one or more pressure transducers through a single manifold 214. Manifold 214 also interfaces with the blood pressure cuff port 230.

In embodiments, the example carrier assembly 200 provides a single part that provides mounting for the pump 202 and valves 206. In some embodiments, the example carrier assembly 200 includes features for managing electrical wire routing for the pump and valve wires, such as harnesses, slots, snaps, mounts, ports, and other components known in the art. Wire routing feature 208 and integrated pump/valve harness 220 are examples of features for managing wire routing for the pump and valve wires.

In some embodiments, the example carrier assembly 200 includes mounts for a speaker 212, a WiFi radio 210 and/or a Bluetooth radio 218. The mounts can include slots in the assembly 200, harnesses, snaps, recesses, or other components known in the art.

Figure 17:
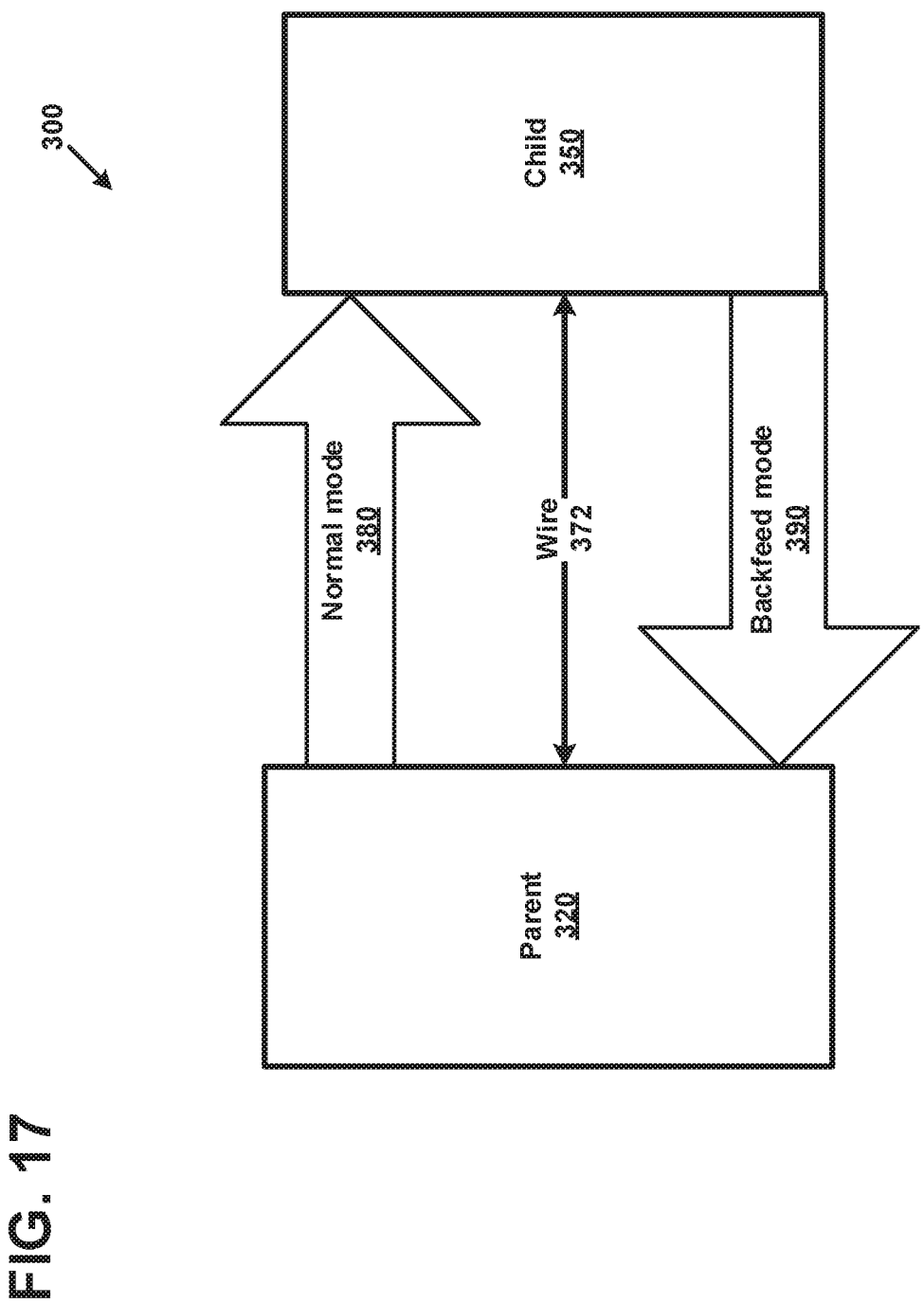
FIG. 17 is a block diagram of an example power management system.
Figure 18:
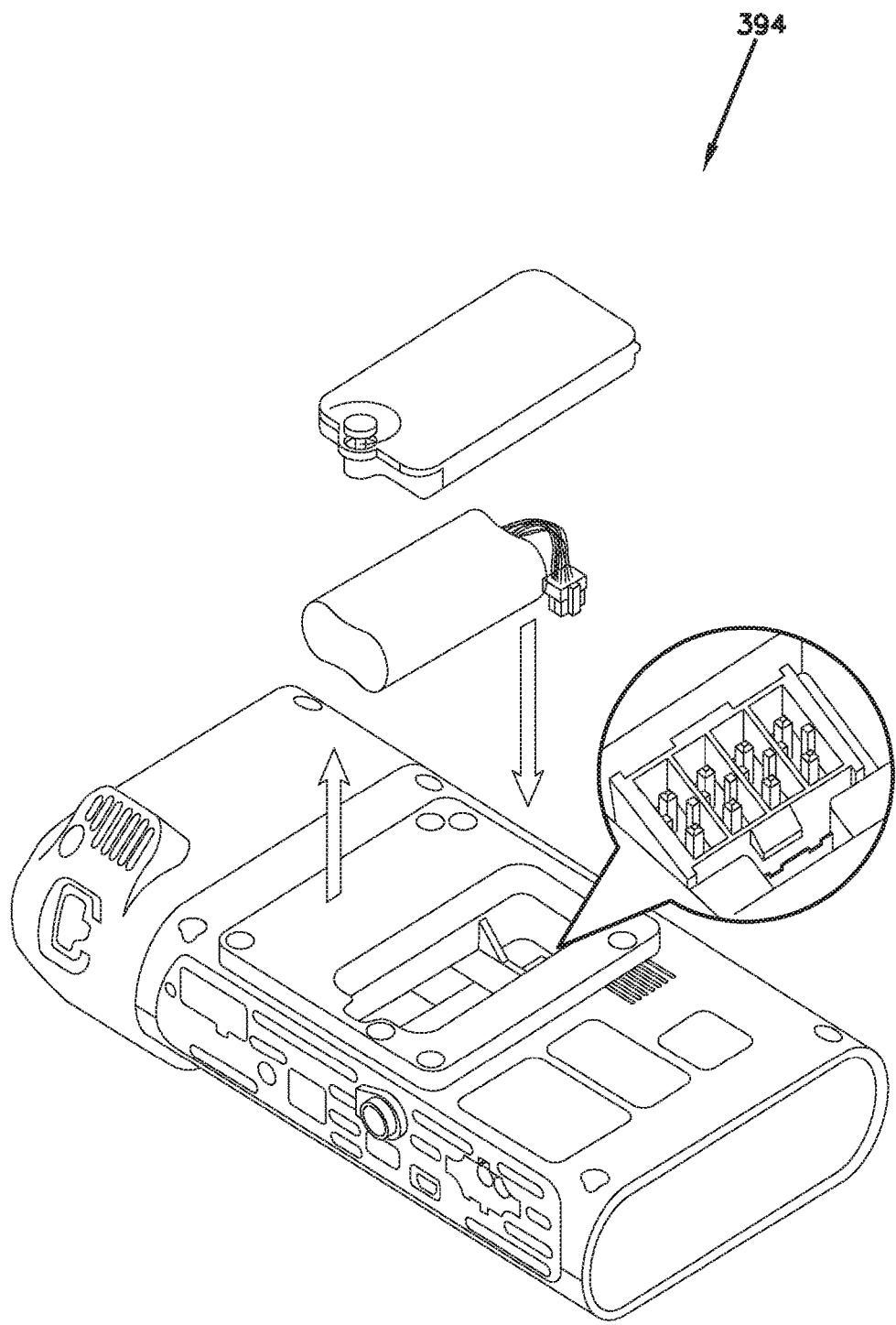
FIG. 18 illustrates an embodiment of a child module in the example power management system shown in FIGS. 6 and 17.
Figure 19:
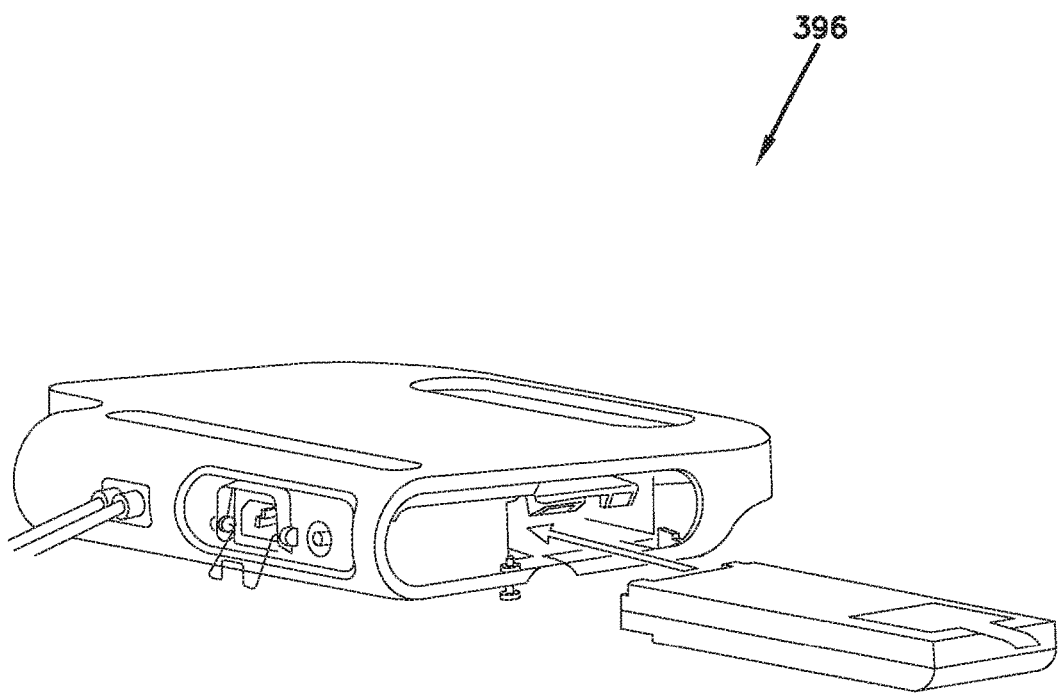
FIG. 19 illustrates an embodiment of a parent module in the example power management system shown in FIGS. 6 and 17.

FIGS. 6 and 17-19 illustrate an example power management system 300. The example system 300 includes a parent module 320 and a child module 350, each with input power connectors and connected by wire 372. Parent module 320 and child module 350 are the medical devices shown in FIGS. 2 and 3, although the example power management system 300 can be used in other environments. Power management system 300 extends the operational time beyond the battery capacity of the parent module 320. In embodiments, the child input power connector has exposed pins when the connector is unconnected. An embodiment of example child module 394 is shown in FIG. 18 and an embodiment of example parent module 396 is shown in FIG. 18. Other embodiments can include more or fewer components.

The example system 300 can be configured to run on mains power, wherein the parent module 320 and the child module 350 can be powered indefinitely. In the example system 300, the parent module 320 is responsible for charging the battery of the child module 350 when the child module 350 is not connected to mains power. The parent module 320 can also be responsible for providing operational power to the child module 350. This is depicted in FIG. 17 as normal mode 380: power flowing from parent module 320 to child module 350.

In embodiments, parent module 320 includes a larger battery than child module 350. For example, parent module 320 includes a 9 cell battery and child module 350 includes a 2 cell battery. Other configurations are possible.

In embodiments, when running on battery power, the parent module 320 continues to charge the child module's 350 battery. This is shown as normal mode 380 in FIG. 17. In some embodiments, it is likely that the child module's 350 battery is powered from the time spent on mains power. In embodiments, the parent module's 320 battery expires. At that point, the example system 300 deploys a backfeed function, shown as backfeed mode 390 in FIG. 17, that allows power to flow both ways in the interface between the parent module 320 and the child module 350. In embodiments, the backfeed mode 390 enables the system to continue to operate on the child module's 350 battery after the parent module's 320 battery is exhausted. In embodiments, this configuration can maximize battery life in contrast to non-backfeed configurations.

In embodiments, the child module 350 can operate standalone. In embodiments, the connector on the child module 350 that connects to the parent module 350 is large enough to expose the connector pin. Exposing a powered pin can produce an unsafe and undesirable situation.

In embodiments, when the child module 350 is not connected to the parent module 320, the child module's 350 system detects that the pin is disconnected. When the system detects that the pin is disconnected, the child module's 350 system de-energizes the power pin on the child module 350.

A wire 372 used to convey power from the parent module 320 to the child module 350 (normal mode 380) is also used to convey power from the child module 350 to the parent module 320 (backfeed module). A battery life status 124 shown on a display of child module 350, an example embodiment of which is shown in FIG. 3, includes the combined battery life using backfeed mode 390 when the parent module 320 is connected to the child module 350.

The example medical device 104 can also optionally include an electromagnetic interference (EMI) suppression module 400. In some medical devices, sensitive signals in a printed circuit board are buried on inner layers. These signals can go to an external shielded cable. Examples include SpO2, electroencephalograph (EEG), electrocardiograph (ECG), etc. These cables can act as antennas for unwanted electromagnetic interference, such as radio frequency interference (RFI), that is both radiated from and induced into the device.

The example EMI suppression 400 includes applying a ferrite to surround a printed circuit board. In embodiments, the ferrite is wrapped around a bare printed circuit board, or surrounds part of a printed circuit board. In embodiments, the ferrite has a geometry such that it suppresses unwanted RFI on traces on inner and/or outer layers of the printed circuit assembly.

Figure 10:
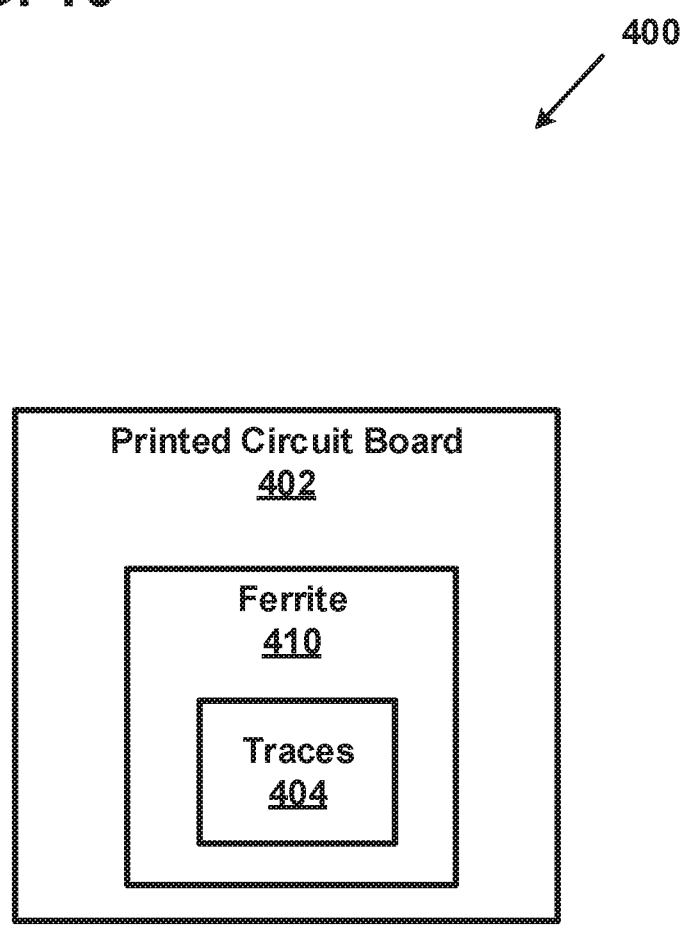
FIG. 10 is a block diagram of an example electromagnetic interference (EMI) suppression system.

FIG. 10 is a schematic block diagram of an embodiment of EMI suppression 400. Ferrite 410 is used to surround traces 404 in printed circuit board 402. The traces 404 do not directly connect to the ferrite 410. Rather, the traces 404 surrounded by ferrite 410 are routed to stay within the printed circuit board 402 and do not come up to the surface of printed circuit board 402. Generally, signals in traces are not interrupted by layer transitions or impedance mismatches. When passing through ferrite 410, the traces 404 do not transition from their electrical shielding.

Figure 11:
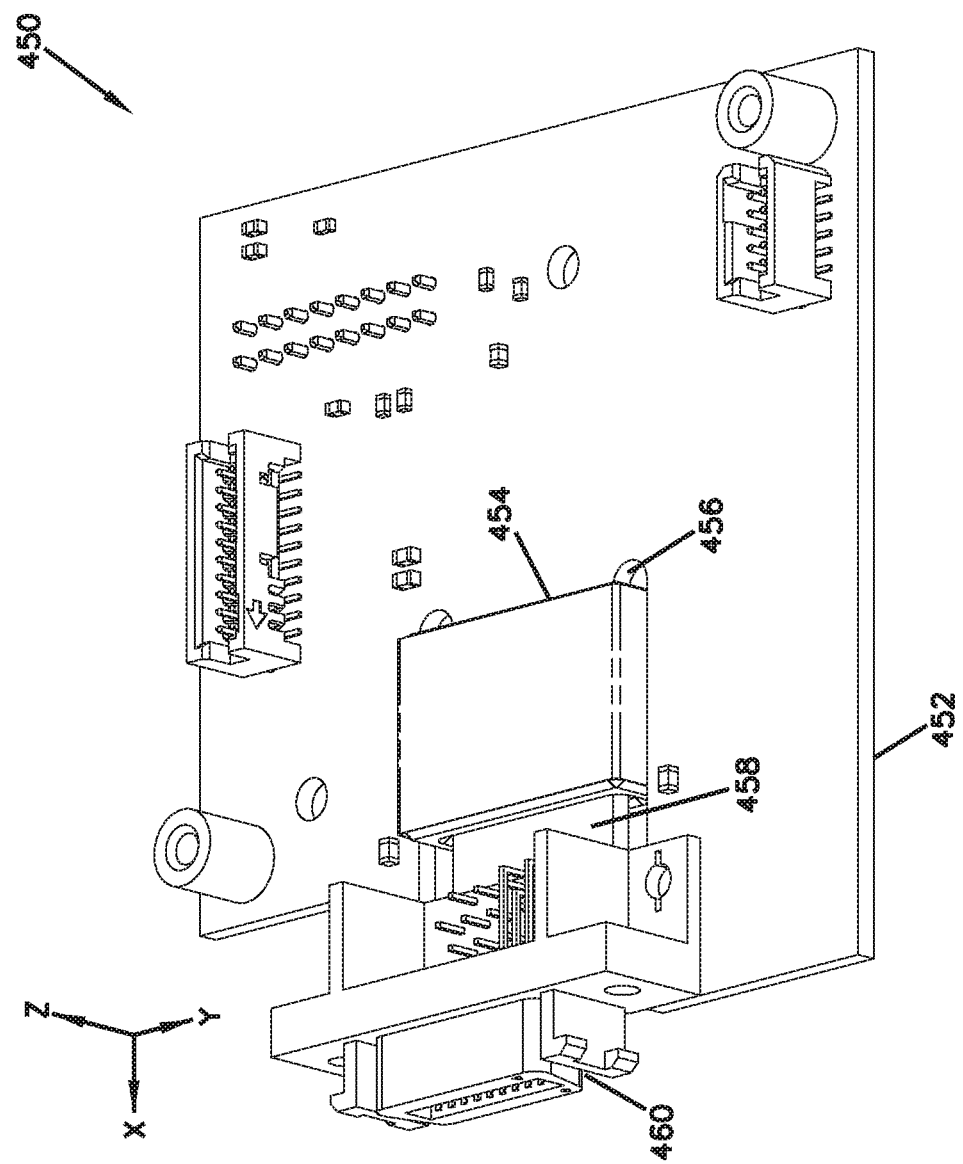
FIG. 11 illustrates an embodiment of the example EMI suppression system shown in FIG. 10.

FIG. 11 illustrates a perspective view of an embodiment of the example EMI suppression 450 discussed in connection with FIG. 10. EMI suppression 450 includes slots 456 in a PCB 452 that define tongue 458, and ferrite 454 surrounding a portion of the PCB 452 containing traces 470. The tracings 470 are shown in phantom form to indicate that the tracings are actually below the surface of the PCB 452 in one of the inner layers. A cable connector 460 is also depicted. Other embodiments can include more or fewer components.

Figure 12:
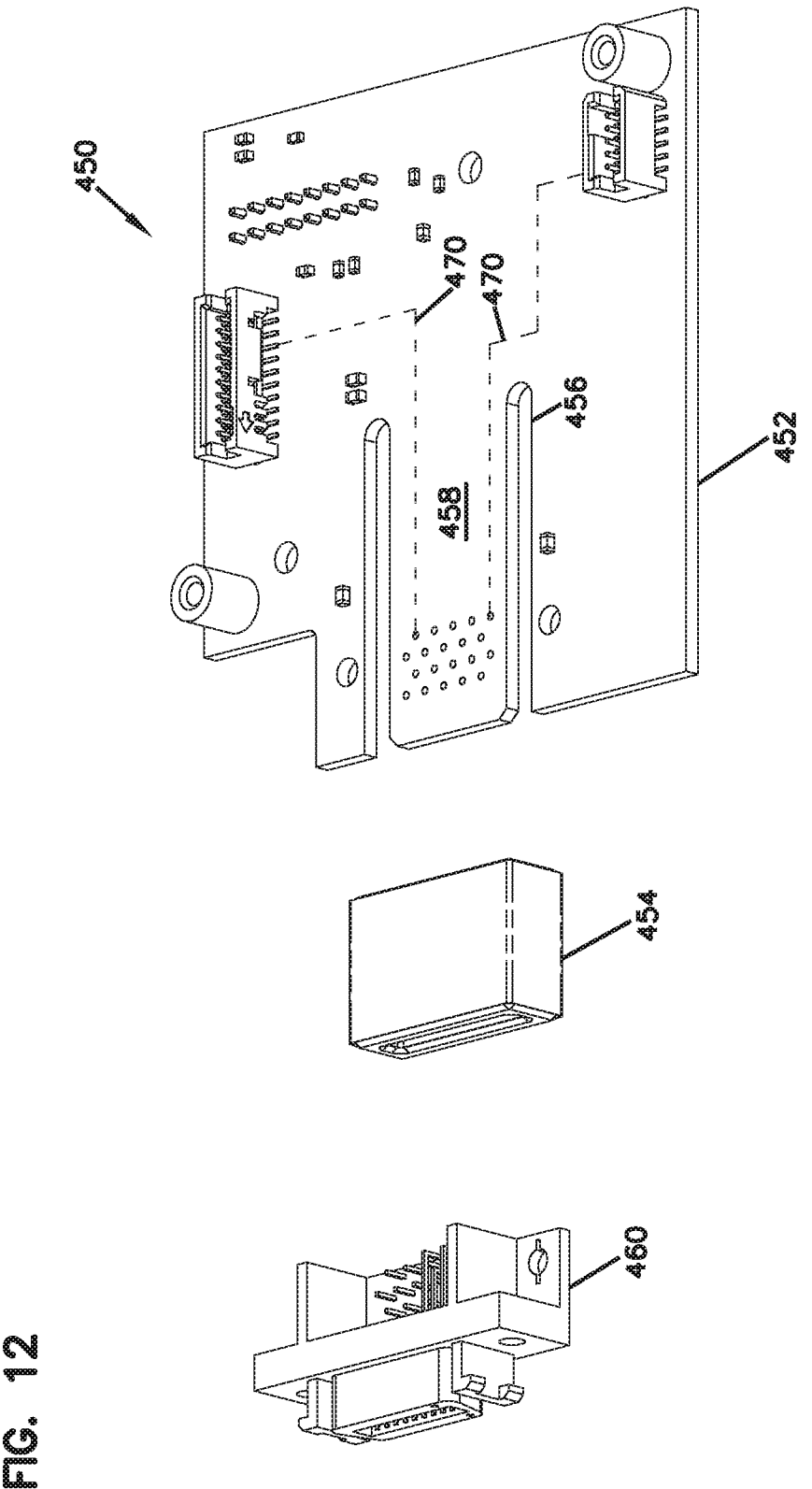
FIG. 12 illustrates an exploded view of the embodiment of the example EMI suppression system shown in FIG. 11.
Figure 13:
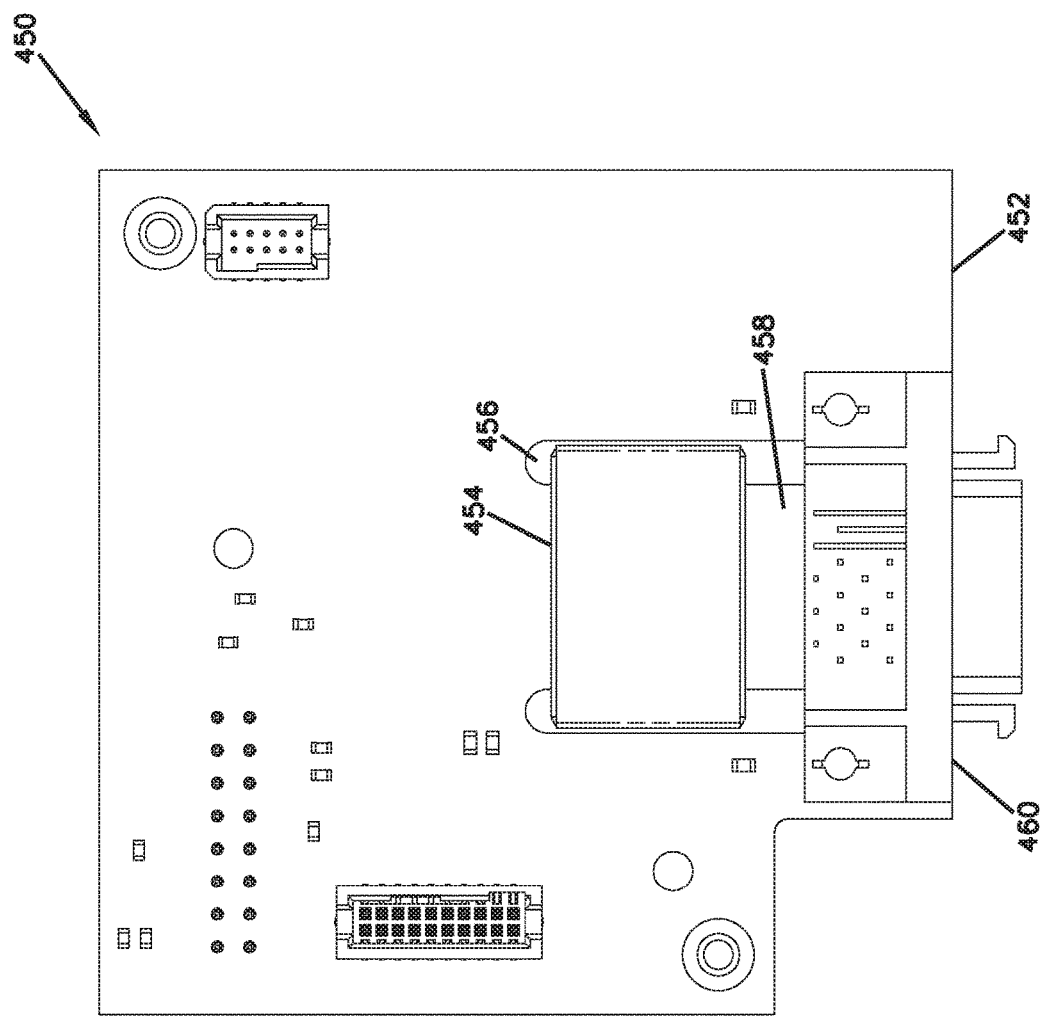
FIG. 13 illustrates a top plan view of the embodiment of the example EMI suppression system shown in FIG. 11.
Figure 14:
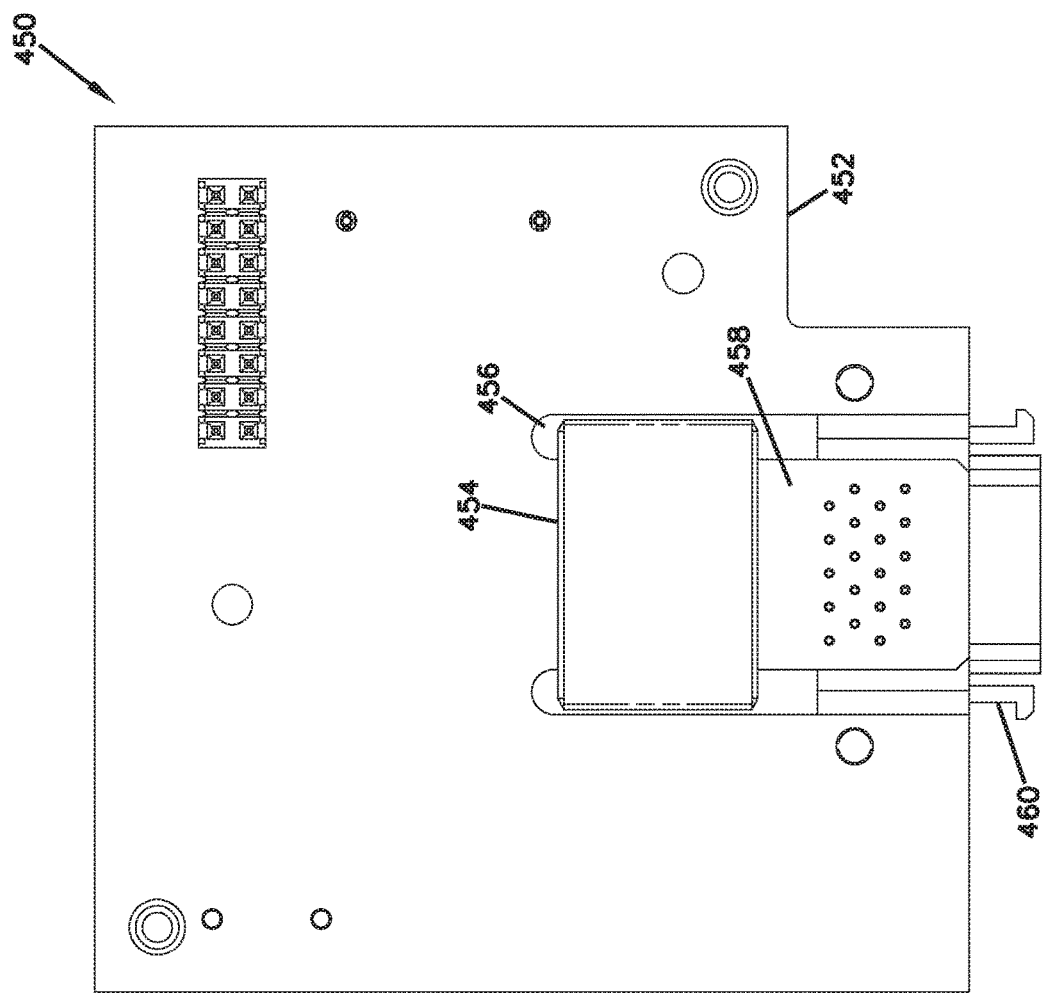
FIG. 14 illustrates a bottom plan view of the embodiment of the example EMI suppression system shown in FIG. 11.
Figure 15:
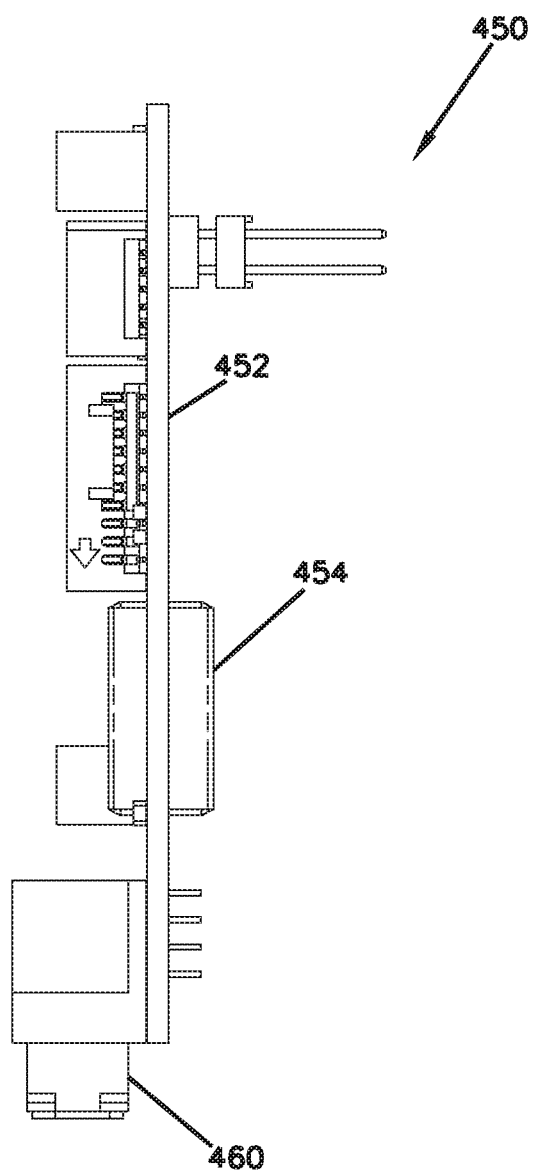
FIG. 15 illustrates a right side view of the embodiment of the example EMI suppression system shown in FIG. 11.
Figure 16:
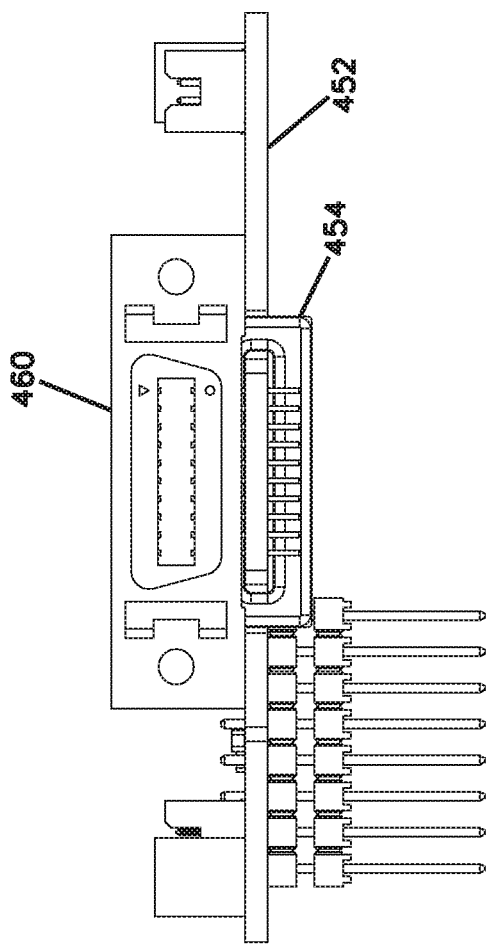
FIG. 16 illustrates a front view of the embodiment of the example EMI suppression system shown in FIG. 11.

FIGS. 12-16 additionally illustrate various views of the embodiment of the example EMI suppression 450 shown in FIG. 11. Specifically, FIG. 12 is an exploded, perspective view of EMI suppression 450, FIG. 13 is a top plan view of EMI suppression 450, FIG. 14 is a bottom plan view of EMI suppression 450, FIG. 15 is a right side view of EMI suppression 450, and FIG. 16 is a front view of EMI suppression 450. Unless otherwise noted, the following discussion is with reference to FIGS. 11-16.

Surrounding traces 470 with ferrite 454 provides EMI suppression even in embodiments where a cord connecting to printed circuit board 452 does not include EMI suppression components. Although EMI suppression 450 is discussed in relation to a medical device, it can be used to suppress EMI in any PCB with a cable connection, regardless of the application.

Ferrite 454 has an annular cross-section thereby enabling it to pass through tongue 458 and surround traces within PCB 452. In the embodiment shown, ferrite 454 has a rectangular annulus cross-section, although other shapes are possible. Ferrite 454 is positioned on the distal end of tongue 458 adjacent to the connector assembly 460. In embodiments, EMI suppression improves as ferrite 454 is positioned closer to connector assembly 460. However, any position of ferrite 454 on tongue 458 provides EMI suppression.

Ferrite 454 is positioned over the PCB 452 before soldering near the cable connector 460. Ferrite 454 can be secured to the PCB 452 using, for example, cloth tape.

Cable connector 460 can connect to, and receive data from, a vital signs device, such as an SpO2 monitor, an EEG, or other device.

In the embodiment shown, ferrite 454 has a single-piece construction. Other embodiments are contemplated where ferrite 454 is formed by more than one piece.

Ferrite 454 surrounds the tracings within PCB 452 in at least the x-y planes above and below PCB 452 as well as the x-z planes. In embodiments, traces 470 carry signals that might be sensitive to noise, such as EMI, which could damage the signal's integrity. An example of a signal sensitive to noise is a peripheral capillary oxygen saturation (SpO2) signal.

An example installation of the example EMI suppression was conducted and reduced EMI. In the example installation, a printed circuit was carved to accept a standard Ferrite. Then the cable connector was removed. Ferrite was inserted and then the connector was replaced.

Figure 22:
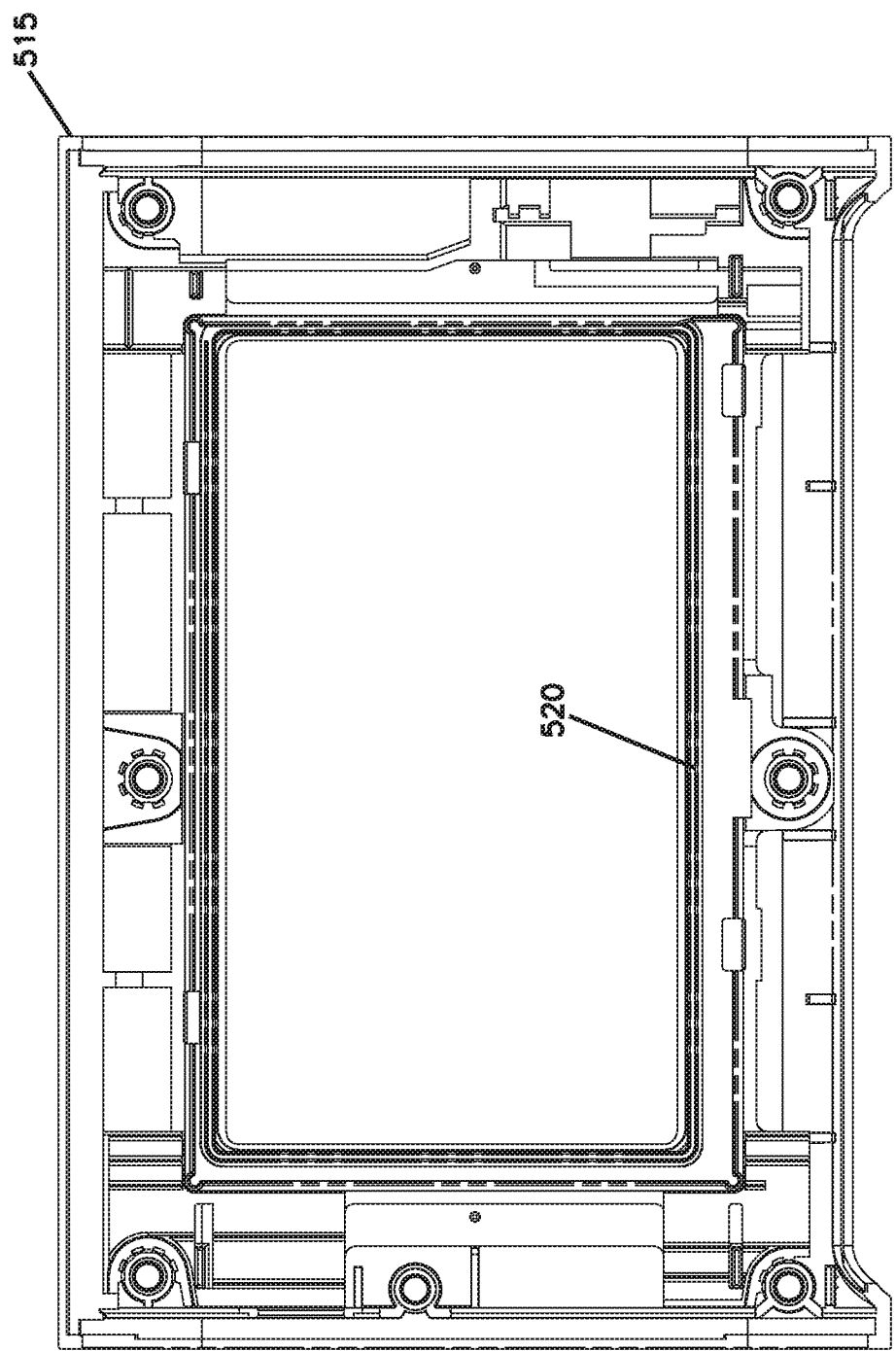
FIG. 22 illustrates a rear plan view of an embodiment of example front housing.
Figure 23:
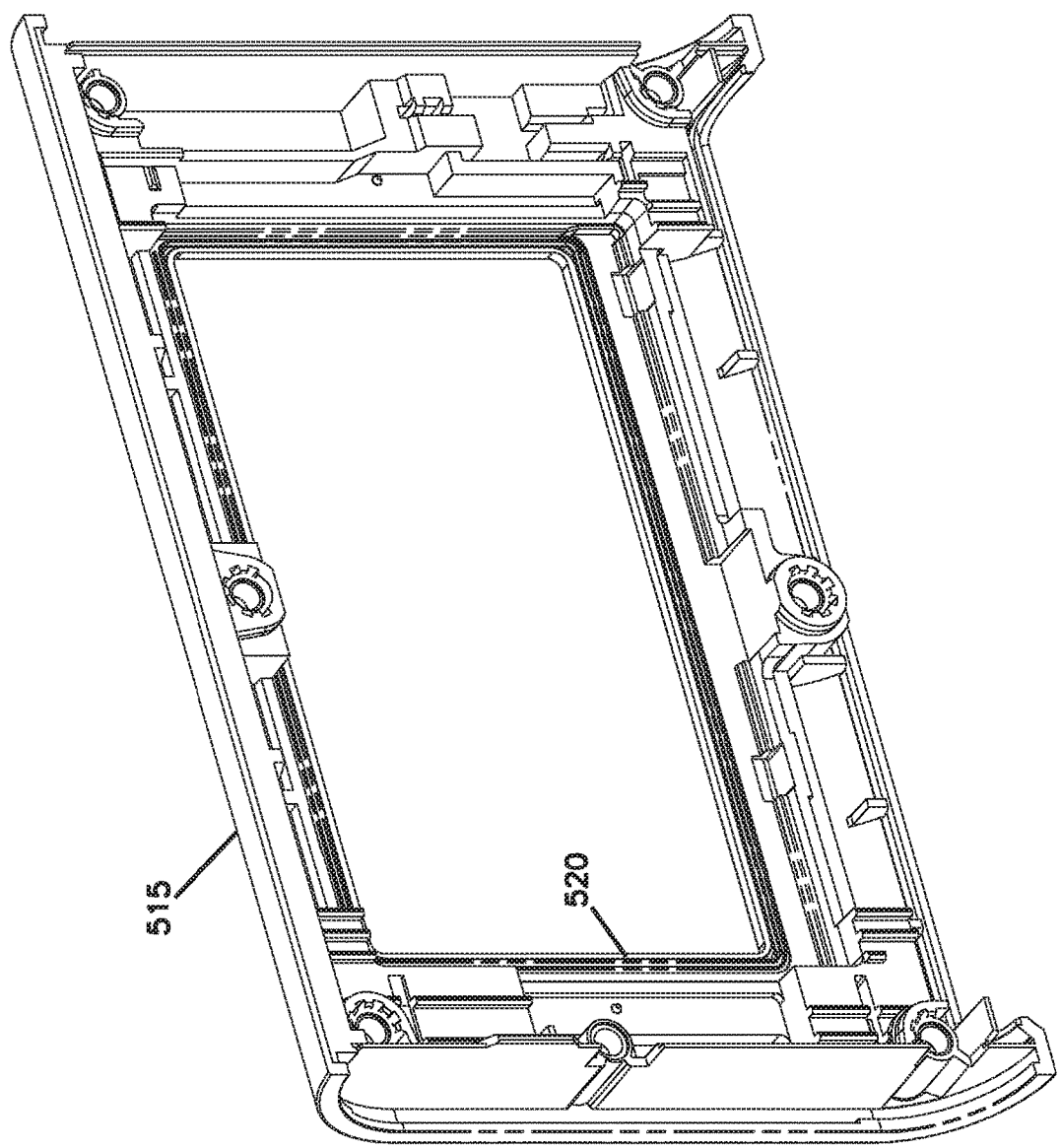
FIG. 23 illustrates a rear perspective view of the embodiment of example front housing shown in FIG. 22.
Figure 24:
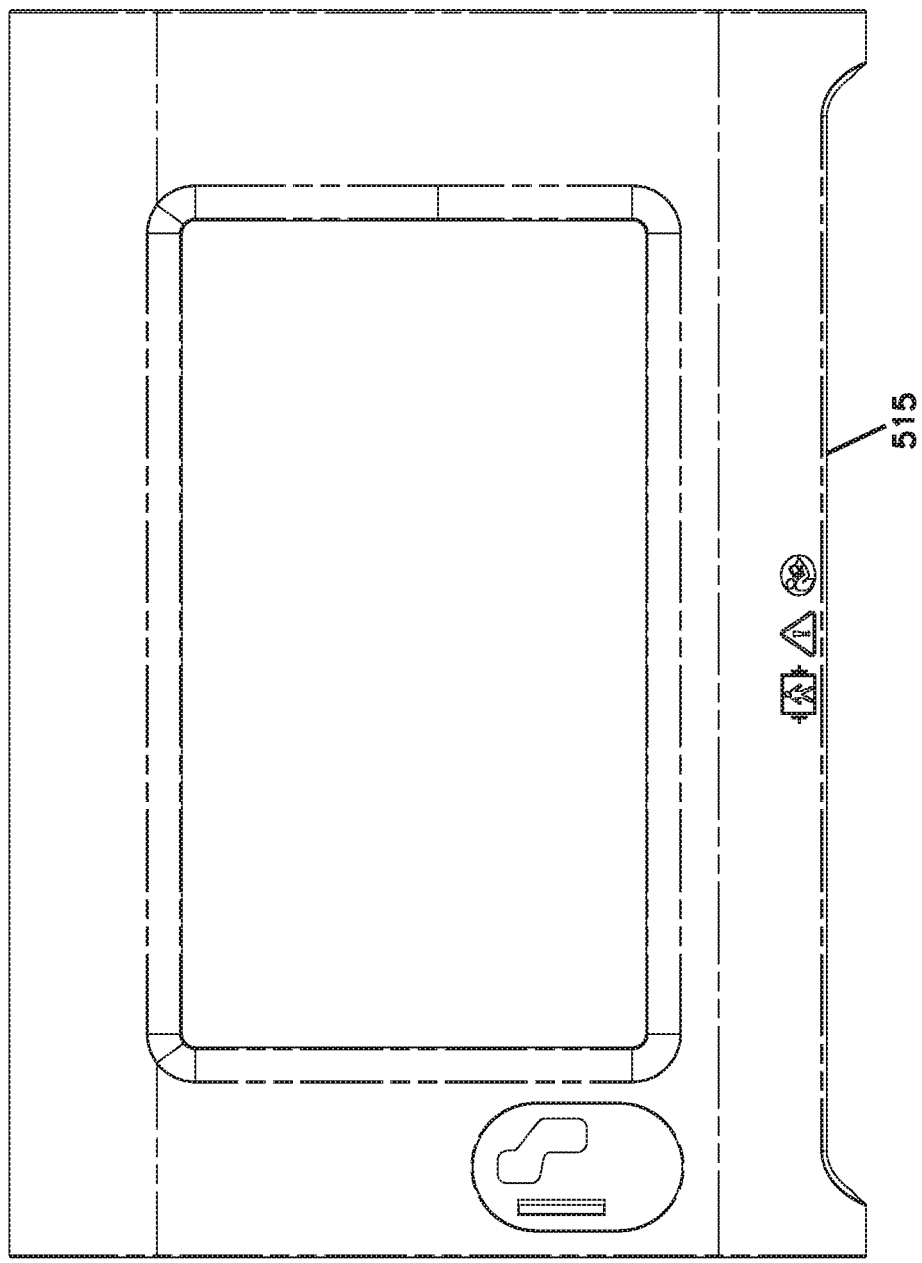
FIG. 24 illustrates a front plan view of the embodiment of example front housing shown in FIG. 22.
Figure 25:
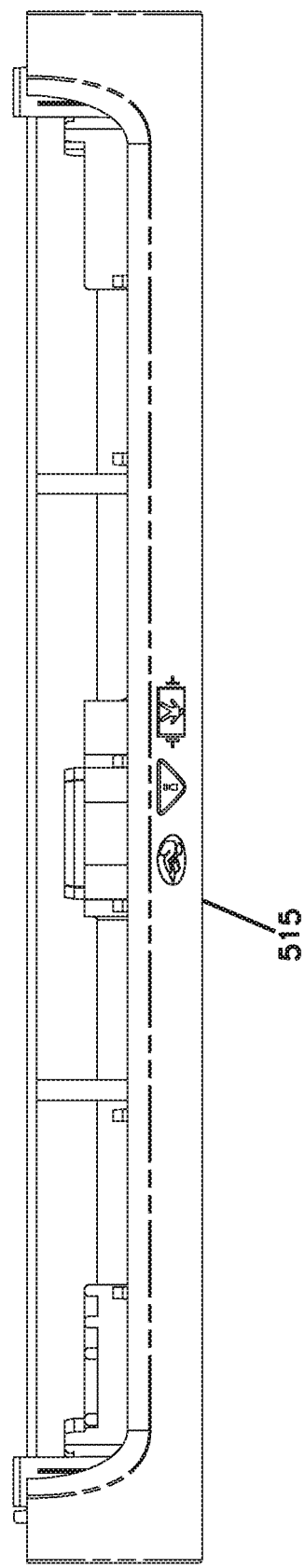
FIG. 25 illustrates a bottom plan view of the embodiment of example front housing shown in FIG. 22.
Figure 26:
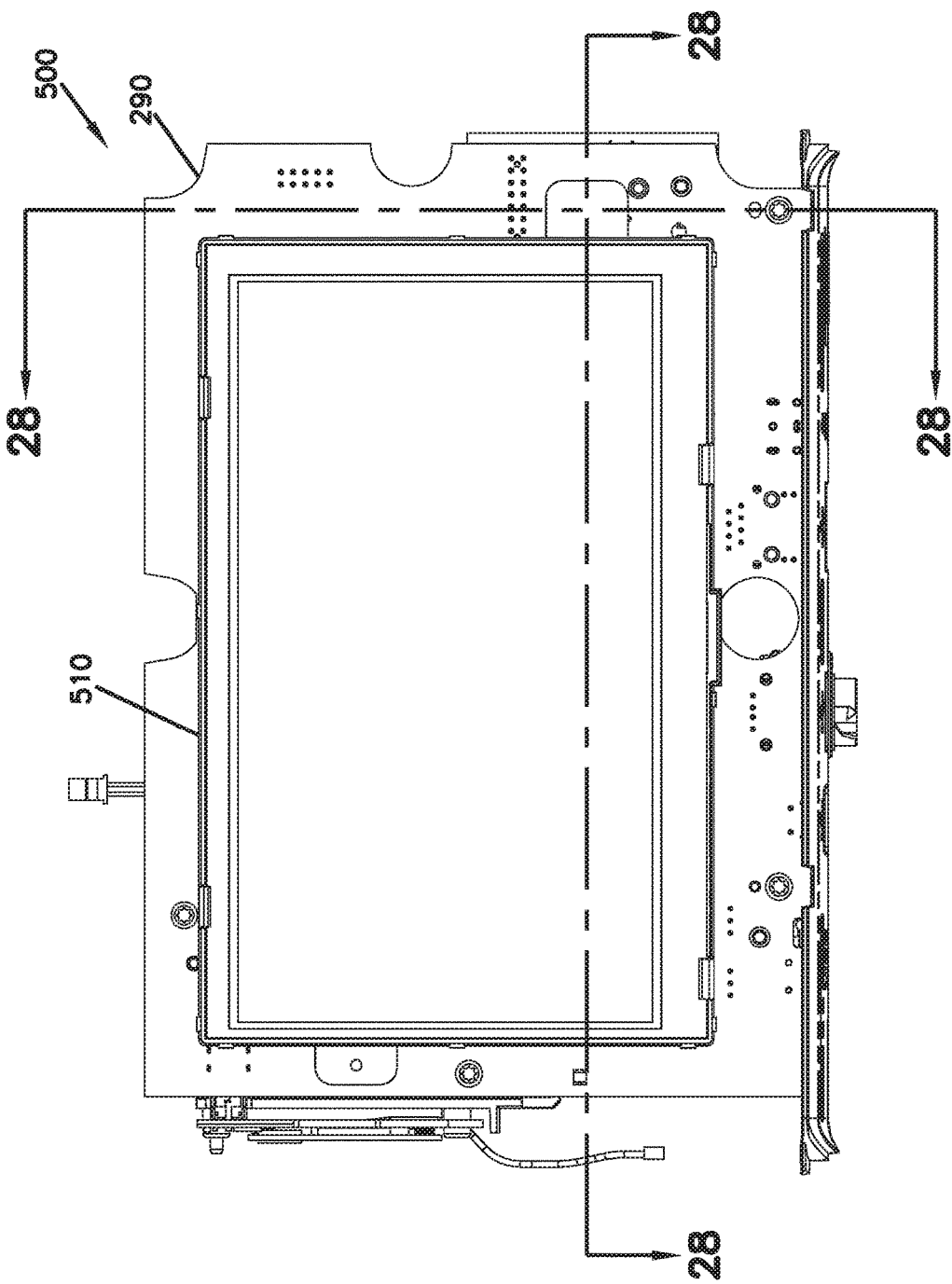
FIG. 26 illustrates an embodiment of an example liquid crystal display (LCD) assembly mounted to a printed circuit assembly (PCA).
Figure 27:
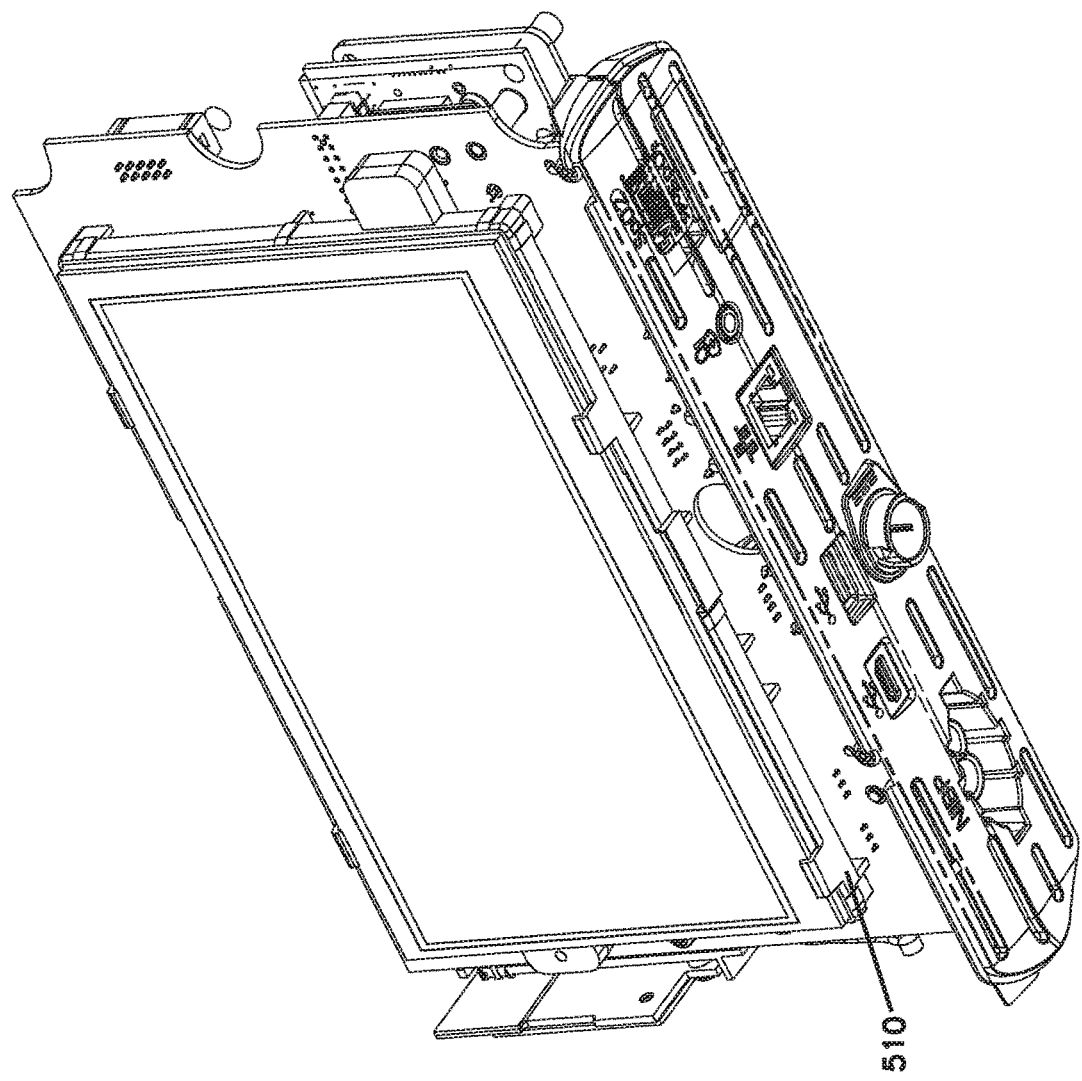
FIG. 27 illustrates a front perspective view of the embodiment of example LCD assembly mounted to the PCA.
Figure 28:
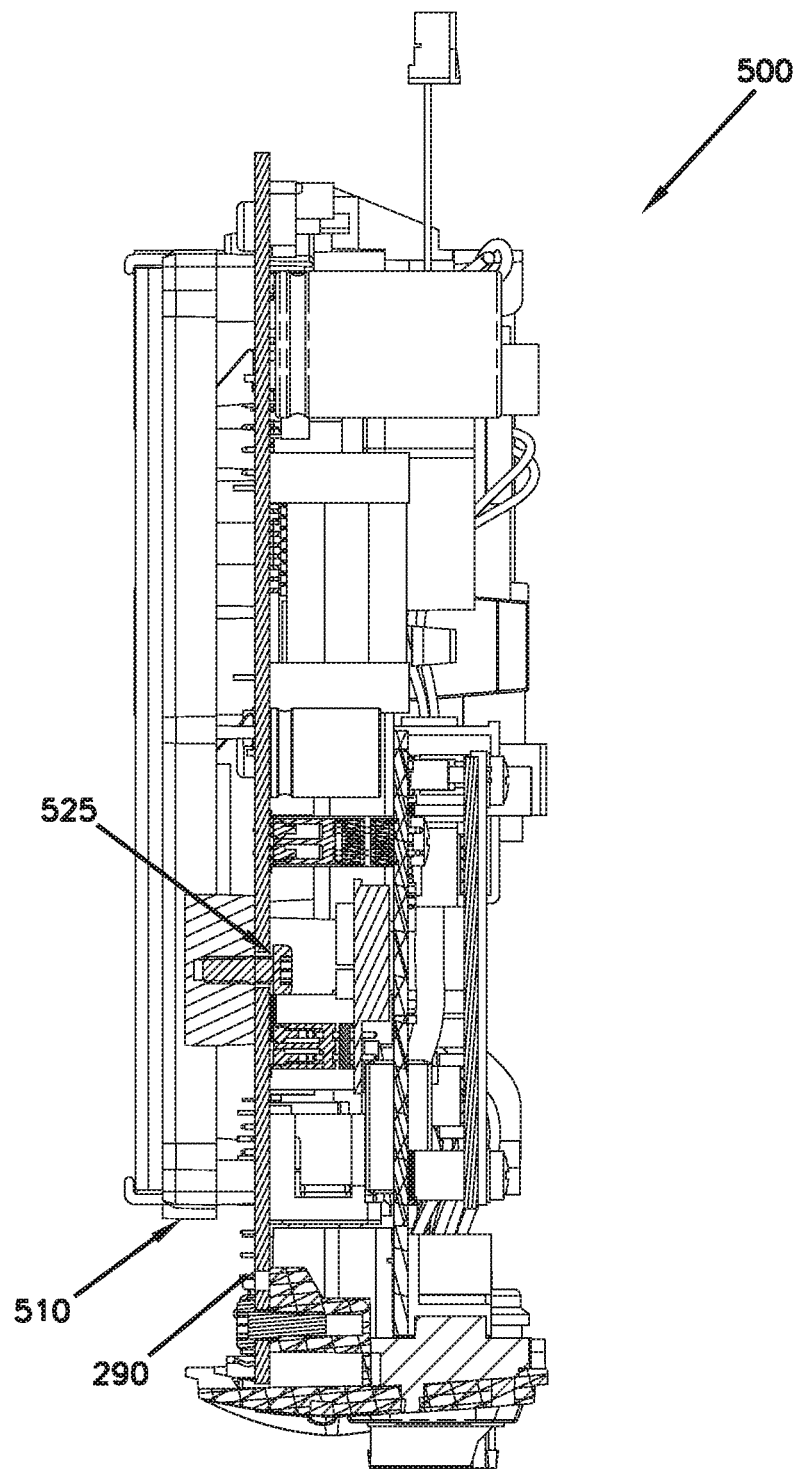
FIG. 28 illustrates a side view, along axis A-A in FIG. 26, of the embodiment of example LCD assembly mounted to the PCA.
Figure 29:
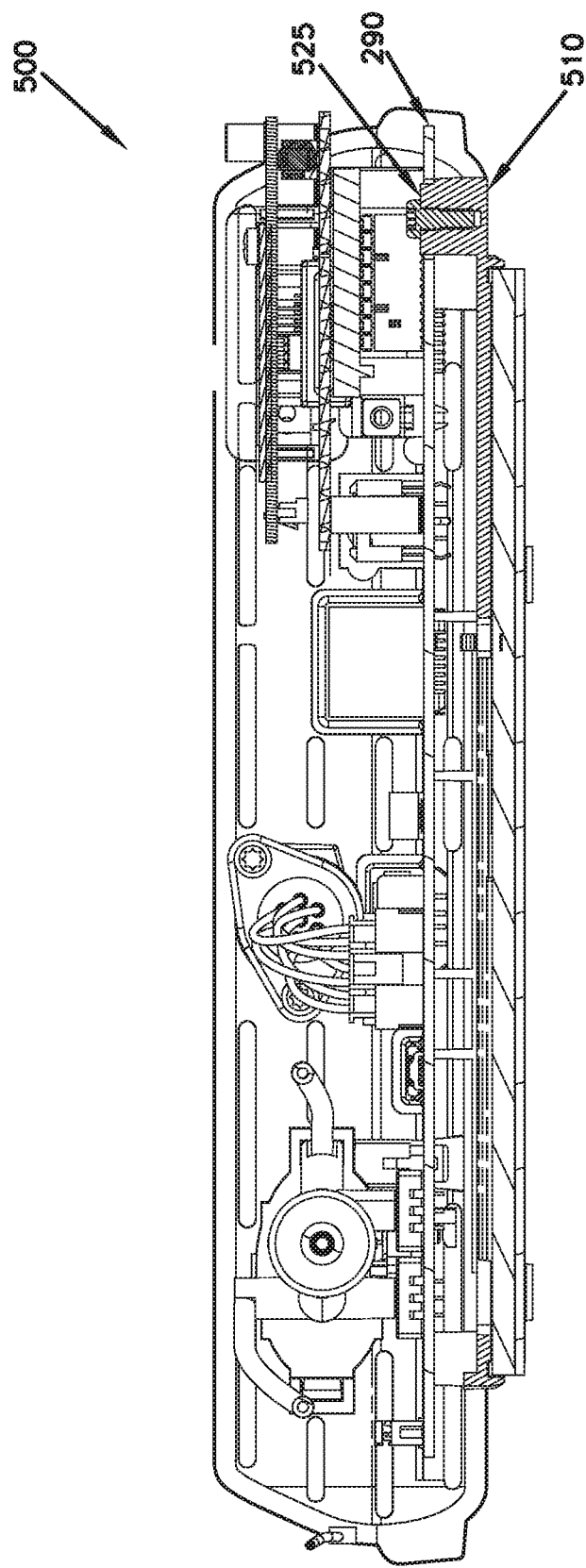
FIG. 29 illustrates a top view, along axis B-B in FIG. 26, of the embodiment of example LCD assembly mounted to the PCA.

FIGS. 7, 8, and 22-29 illustrate an example display 500. The example display 500 includes a printed circuit assembly (PCA) 290, a liquid crystal display (LCD) assembly 510, a front housing 515, an elastomeric bezel 520, obround slots 524 and an obround boss 525. A rear housing, not shown, mates with the front housing 515 and PCA 290. Front housing 515 is also shown in FIGS. 22-25: FIG. 22 is a rear plan view of front housing 515, FIG. 23 is a rear perspective view of the front housing 515, FIG. 24 is a front plan view of the front housing 515, and FIG. 25 is a bottom plan view of the front housing 515. Printed circuit assembly 290 and LCD assembly 510 are additionally shown in FIGS. 26-29: FIG. 26 is a front plan view of PCA 290 and LCD assembly 510, FIG. 27 is a bottom front perspective view of PCA 290 and LCD assembly 510, FIG. 28 is a side view along axis A-A in FIG. 26, and FIG. 29 is a top view along axis B-B in FIG. 26. Other example displays can include more or fewer components than those depicted.

The example display 500 has an LCD assembly 510 mounted directly to the PCA 290. The mount enables the LCD assembly 510 to float relative to the PCA 290. Because the LCD assembly 510 can float, it can conform to features in the mating front housing/bezel. In embodiments, the floating LCD that interfaces with an elastomeric bezel 520 on the front housing seals the LCD from fluid ingress and it can provide impact resistance.

The example embodiment of the display 500 illustrated in FIGS. 7 and 22-29 shows the LCD assembly 510 fastened to the PCA. The LCD assembly 510 has obround bosses 525 that mate with similarly shaped but larger obround slots 524 in the printed circuit board 290. This clearance can enable the LCD assembly 510 to float in the x- and y-axes relative to the PCA 290. The LCD assembly 510 is thereby secured to the PCA in the z-axis with, for example, screws 526 that thread into the frame bosses 525, where the head diameter of the screw 526 can be larger than the slot width in the PCA 290. In embodiments, the frame bosses 525 are taller than the thickness of the PCA 290 which can prevent the screw 526 head from seating on the PCA 290 and locking the LCD assembly 510 to the PCA 290. This is illustrated in the cut-out view shown in FIG. 8, where the frame boss 525 is seen extending through the obround slot 524 and beyond the PCA 290 because the frame boss 525 is taller than the thickness of the PCA 290.

Additionally, an elastomeric bezel 520 can be precisely positioned and contained in the front housing 515 relative to the LCD opening, where the bezel 520 can have features that precisely locate the LCD assembly 510. The floating enables the LCD to be positioned to the LCD opening in the front housing independent of the location of the PCA, which can have other design constraints that could add to the tolerance stackup. In embodiments, the bezel 520 is pre-assembled to the front housing 515.

Figure 9:
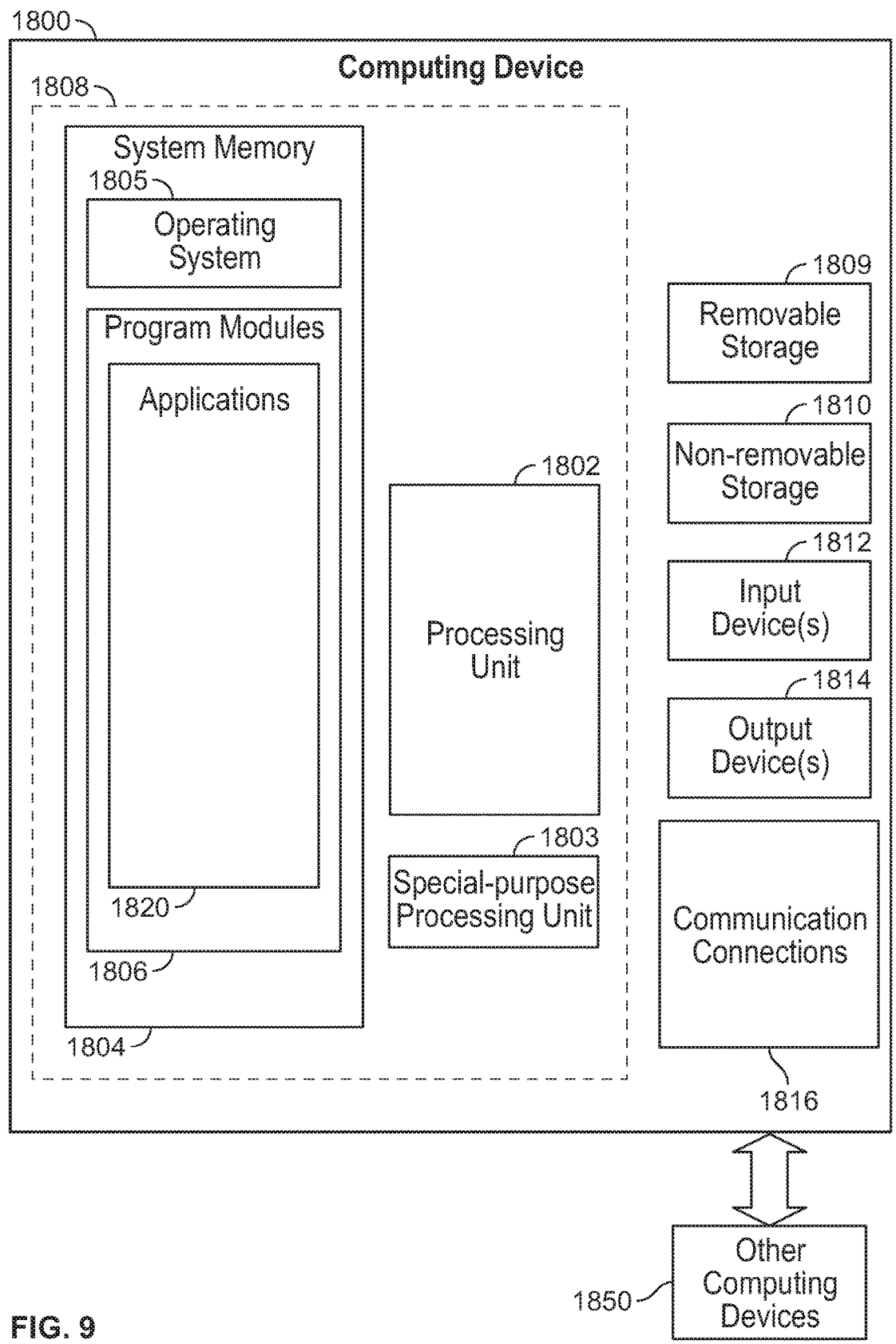
FIG. 9 is a block diagram illustrating physical components of a computing device with which examples and embodiments of the disclosure can be practiced.

FIG. 9 is a block diagram illustrating physical components (i.e., hardware) of a computing device 1800 with which embodiments of the disclosure may be practiced. The computing device components described below may be suitable to act as the computing devices described above, such as wireless computing device and/or medical device of FIG. 1. In a basic configuration, the computing device 1800 may include at least one processing unit 1802, 1803 and a system memory 1804. Depending on the configuration and type of computing device, the system memory 1804 may comprise, but is not limited to, volatile storage (e.g., random access memory), non-volatile storage (e.g., read-only memory), flash memory, or any combination of such memories. The system memory 1804 may include an operating system 1805 and one or more program modules 1806 suitable for running software applications 1820. The operating system 1805, for example, may be suitable for controlling the operation of the computing device 1800. Furthermore, embodiments of the disclosure may be practiced in conjunction with a graphics library, other operating systems, or any other application program and is not limited to any particular application or system. This basic configuration is illustrated in FIG. 9 by those components within a dashed line 1808. The computing device 1800 may have additional features or functionality. For example, the computing device 1800 may also include additional data storage devices (removable and/or non-removable) such as, for example, magnetic disks, optical disks, or tape. Such additional storage is illustrated in FIG. 9 by a removable storage device 1809 and a non-removable storage device 1810.

As stated above, a number of program modules and data files may be stored in the system memory 1804. While executing on the processing unit 1802, the program modules 1806 may perform processes including, but not limited to, generate list of devices, broadcast user-friendly name, broadcast transmitter power, determine proximity of wireless computing device, connect with wireless computing device, transfer vital sign data to a patient's EMR, sort list of wireless computing devices within range, and other processes described with reference to the figures as described herein. Other program modules that may be used in accordance with embodiments of the present disclosure, and in particular to generate screen content, may include electronic mail and contacts applications, word processing applications, spreadsheet applications, database applications, slide presentation applications, drawing or computer-aided application programs, etc.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. For example, embodiments of the disclosure may be practiced via a system-on-a-chip (SOC) where each or many of the components illustrated in FIG. 9 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, may be operated via application-specific logic integrated with other components of the computing device 1800 on the single integrated circuit (chip). Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

The computing device 1800 may also have one or more input device(s) 1812 such as a keyboard, a mouse, a pen, a sound or voice input device, a touch or swipe input device, etc. The output device(s) 1814 such as a display, speakers, a printer, etc. may also be included. The aforementioned devices are examples and others may be used. The computing device 1800 may include one or more communication connections 1816 allowing communications with other computing devices 1850. Examples of suitable communication connections 1816 include, but are not limited to, RF transmitter, receiver, and/or transceiver circuitry; universal serial bus (USB), parallel, and/or serial ports.

The term computer readable media as used herein may include non-transitory computer storage media. Computer storage media may include volatile and nonvolatile, removable and non-removable media implemented in any method or technology for storage of information, such as computer readable instructions, data structures, or program modules. The system memory 1804, the removable storage device 1809, and the non-removable storage device 1810 are all computer storage media examples (i.e., memory storage.) Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 1800. Any such computer storage media may be part of the computing device 1800. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Although the example medical devices described herein are devices used to monitor patients, other types of medical devices can also be used. For example, the different components of the CONNEX™ system, such as the intermediary servers that communication with the monitoring devices, can also require maintenance in the form of firmware and software updates. These intermediary servers can be managed by the systems and methods described herein to update the maintenance requirements of the servers.

Embodiments of the present invention may be utilized in various distributed computing environments where tasks are performed by remote processing devices that are linked through a communications network in a distributed computing environment.

The block diagrams depicted herein are just examples. There may be many variations to these diagrams described therein without departing from the spirit of the disclosure. For instance, components may be added, deleted or modified.

While embodiments have been described, it will be understood that those skilled in the art, both now and in the future, may make various improvements and enhancements can be made.

What is claimed is:

1. A printed circuit board assembly, comprising:
    a printed circuit board, comprising:
        a plurality of traces;
        two slots defining a tongue portion of the printed circuit board;
        a substantially planar top surface; and
        a substantially planar bottom surface; and
    a ferrite having an annular cross section defining a channel,
        wherein the ferrite extends through the two slots and is positioned on and surrounds at least part of the tongue portion of the printed circuit board, such that a portion of the plurality of traces passes through the channel of the ferrite.

2. The printed circuit board assembly of claim 1, wherein the annular cross section is formed by two separate pieces that are joined together.

3. The printed circuit board assembly of claim 1, wherein the annular cross section is substantially rectangular.

4. A medical device, comprising:
    a housing; and
    a printed circuit board assembly supported by the housing, the printed circuit board assembly comprising:
        a printed circuit board including a plurality of traces and two slots defining a tongue portion,
            wherein the printed circuit board has a substantially planar top surface and a substantially planar bottom surface; and
            wherein at least some of the plurality of traces carry sensitive signals;
        a ferrite extending through the two slots and surrounding at least part of the tongue portion, the ferrite having an annular cross section, the annular cross section defining a channel,
            wherein the ferrite is positioned on the tongue portion such that a portion of the plurality of traces passes through the channel.

5. The printed circuit board assembly of claim 1, further comprising a connector assembly
    positioned on a distal end of the tongue portion,
    wherein the ferrite is positioned on the distal end of the tongue portion.

6. The printed circuit board assembly of claim 5, wherein at least some of the plurality of traces carry a sensitive signal, and
    wherein, when the plurality of traces pass through the channel, the plurality of traces are positioned between the substantially planar top surface and the substantially planar bottom surface of the printed circuit board.

7. The printed circuit board assembly of claim 6, wherein the sensitive signal includes vital signs data.

8. The printed circuit board assembly of claim 7, wherein the connector assembly is configured to receive vital signs data from an external device.

9. The printed circuit board assembly of claim 1, further comprising a plurality of mounting elements configured to mate with a plurality of complementary mounting elements positioned on a medical device main assembly.

10. A medical device, comprising:
    a printed circuit board assembly in communication, the printed circuit board assembly comprising:
        a printed circuit board including a plurality of traces, a tongue portion defined by two slots in the printed circuit board, a substantially planar top surface and a substantially planar bottom surface; and
        a ferrite extending through the two slots and surrounding at least part of the tongue portion, the ferrite having a first portion positioned on the substantially planar top surface and a second portion positioned on the substantially planar bottom surface, wherein the ferrite is positioned on the tongue portion of the printed circuit board such that a portion of the plurality of traces passes between the first portion and the second portion.

11. The medical device of claim 10, wherein the first portion of the ferrite is integral with the second portion of the ferrite.

12. The medical device of claim 11, wherein the ferrite has an annular cross section.

13. The medical device of claim 12, wherein a cross section of the ferrite is substantially rectangular annular, an inner surface of the ferrite defining a channel;
   wherein the plurality of traces carry a sensitive signal, and
   wherein, when the plurality of traces pass through the channel, the plurality of traces are positioned between the substantially planar top surface and the substantially planar bottom surface of the printed circuit board.

14. The medical device of claim 13, further comprising a connector assembly
   positioned on a distal end of the tongue portion,
   wherein the ferrite is positioned on the distal end of the tongue portion adjacent to the connector assembly.

15. The medical device of claim 14, wherein the sensitive signal includes vital sign data; and
   wherein the connector assembly is configured to receive vital signs data from an external device.

16. The medical device of claim 15, further comprising a plurality of mounting elements configured to mate with a plurality of complementary mounting elements positioned on a main assembly board.

17. The medical device of claim 4, further comprising a connector assembly
   positioned on a distal end of the tongue portion;
   wherein the ferrite is positioned on the distal end of the tongue portion;
   wherein the annular cross section is substantially rectangular;
   wherein at least some of the plurality of traces carry a sensitive signal including vital signs data, and
   wherein, when the plurality of traces pass through the channel of the ferrite, the plurality of traces do not transition from their electrical shielding.

18. The medical device of claim 17, wherein the connector assembly is configured to connect to a cable connected to a vital signs device.

19. The medical device of claim 18, further comprising a plurality of mounting elements configured to mate with a plurality of complementary mounting elements positioned on a medical device main assembly.

* * * * *